(12) United States Patent
Outtrup et al.

(10) Patent No.: US 6,309,871 B1
(45) Date of Patent: Oct. 30, 2001

(54) POLYPEPTIDES HAVING ALKALINE α-AMYLASE ACTIVITY

(75) Inventors: Helle Outtrup, Vaerlose; Torben Vedel Borchert, Copenhagen; Bjarne Ronfeldt Nielsen, Virum; Vibeke Skovgaard Nielsen, Bagsværd; Lisbeth Hedegaard Hoeck, Skodsborg, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/291,023

(22) Filed: Apr. 13, 1999

(30) Foreign Application Priority Data

Mar. 31, 1999 (DK) ............................................... 1999 00438

(51) Int. Cl.⁷ ...................................................... C12N 9/28
(52) U.S. Cl. .............................................................. 435/202
(58) Field of Search ............................................... 435/202

(56) References Cited

U.S. PATENT DOCUMENTS 3,642,582 * 2/1972 McClary ................................. 195/66

FOREIGN PATENT DOCUMENTS

WO 96/23873 * 8/1996 (WO) .
WO 97/32961 9/1997 (WO) .

OTHER PUBLICATIONS

Igarashi et al. Biochemical and Biophysical Research Communications 248, 372–377 (1998).

Tsukamoto et al. Biochemical and Biophysical Research Communications 151, 25–31 (1988).

* cited by examiner

*Primary Examiner*—Ponnathapu Achutamurthy
*Assistant Examiner*—Kathleen Kerr
(74) *Attorney, Agent, or Firm*—Elias J. Lambiras; Jason I. Garbell

(57) ABSTRACT

The present invention relates to isolated polypeptides having α-amylase activity and isolated nucleic acid sequences encoding the polypeptides, which may be derived from Bacillus. The invention also relates to nucleic acid constructs, vectors, and host cells comprising the nucleic acid sequences as well as methods for producing and using the polypeptides.

6 Claims, 9 Drawing Sheets

```
                                                                    80
707amy  HHNGTNGTMMQYFEWYLPNDGNHWNRLNSDASNLKSKGITAVWIPPAWKGASQNDVGYGAYDLYDLGEFNQKGTVRTKYG
AA-110  HHDGTNGTIMQYFEWNVPNDGQHWNRLHNNAQNLKNAGITAIWIPPAWKGTSQNDVGYGAYDLYDLGEFNQKGTVRTKYG
AA-16   HHDGTNGTIMQYFEWNVPNDGQHWNRLHNNAQNLKNAGITAIWIPPAWKGTSQNDVGYGAYDLYDLGEFNQKGTVRTKYG
BAN     ....VNGTLMQYFEWYTPNDGQHWKRLQNDAEHLSDIGITAVWIPPAYKGLSQSDNGYGPYDLYDLGEFQQKGTVRTKYG
BSG     A.APFNGTMMQYFEWYLPDDGTLWTKVANEANNLSSLGITALWIPPAYKGTSRSDVGYGVYDLYDLGEFNQKGTVRTKYG
AP1378  HHNGTNGTMMQYFEWHLPNDGNHWNRLRDDAANLKSKGITAVWIPPAWKGTSQNDVGYGAYDLYDLGEFNQKGTVRTKYG
SP690   HHNGTNGTMMQYFEWYLPNDGNHWNRLRDDAANLKSKGITAVWIPPAWKGTSQNDVGYGAYDLYDLGEFNQKGTVRTKYG
SP722   HHNGTNGTMMQYFEWHLPNDGNHWNRLRDDASNLRNRGITAIWIPPAWKGTSQNDVGYGAYDLYDLGEFNQKGTVRTKYG
Term    AN..LNGTLMQYFEWYMPNDGQHWRRLQNDSAYLAEHGITAVWIPPAYKGTSQADVGYGAYDLYDLGEFHQKGTVRTKYG 81                                                                  160
707amy  TRSQLQAAVTSLKNNGIQVYGDVVMNHKGGADATEMVRAVEVNPNNRNQEVTGEYTIEAWTRFDFPGRGNTHSSFKWRWY
AA-110  TKAELERAIRSLKANGIQVYGDVVMNHKGGADFTERVQAVEVNPQNRNQEVSGTYQIEAWTGFNFPGRGNQHSSFKWRWY
AA-16   TKAELERAIRSLKANGIQVYGDVVMNHKGGADFTERVQAVEVNPQNRNQEVSGTYEIEAWTGFNFPGRGNQHSSFKWRWY
BAN     TKSELQDAIGSLHSRNVQVYGDVVLNHKAGADATEDVTAVEVNPQNRNQETSEEYQIKAWTDFRFPGRGNTYSDFKWHWY
BSG     TKAQYLQAIQAAHAAGMQVYADVVFDHKGGADGTEWVDAVEVNPSDRNQEISGTYQIQAWTKFDFPGRGNTYSSFKWRWY
AP1378  TRSQLQGAVTSLKNNGIQVYGDVVMNHKGGADGTEMVNAVEVNRSNRNQEISGEYTIEAWTKFDFPGRGNTHSNFKWRWY
SP690   TRNQLQAAVTSLKNNGIQVYGDVVMNHKGGADGTEIVNAVEVNRSNRNQETSGEYAIEAWTKFDFPGRGNNHSNFKWRWY
SP722   TRSQLESAIHALKNNGVQVYGDVVMNHKGGADATENVLAVEVNPNNRNQEISGDYAIEAWTKFDFPGRGNTYSDFKWRWY
Term    TKGELQSAIKSLHSRDINVYGDVVINHKGGADATEDVTAVEVDPADRNRVISGEHLIKAWTHFHFPGRGSTYSDFKWHWY 161                                                                 240
707amy  HFDGVDWDQSRRLNNRIYKFRGHGKAWDWEVDTENGNYDYLMYADIDMDHPEVVNELRNWGNWYTNTLGLDGFRIDAVKH
AA-110  HFDGTDWDQSRQLANRIYKFRGDGKAWDWEVDTENGNYDYLMYADVDMDHPEVINELNRWGVWYANTLNLDGFRLDAVKH
AA-16   HFDGTDWDQSRQLSNRIYKFRGDGKAWDWEVDTENGNYDYLMYADVDMNHPEVINELNRWGVWYANTLNLDGFRLDAVKH
BAN     HFDGADWDESRKIS.RIFKFRGEGKAWDWEVSSENGNYDYLMYADVDYDHPDVVAETKKWGIWYANELNLDGFRIDAAKH
BSG     HFDGVDWDESRKLS.RIYKFRGIGKAWDWEVDTENGNYDYLMYADLDMDHPEVVTELKNWGKWYVNTTNIDGFRLDAVKH
AP1378  HFDGTDWDQSRQLQNKIYKFRGTGKAWDWEVDIENGNYDYLMYADIDMDHPEVINELRNWGVWYTNTLNLDGFRIDAVKH
SP690   HFDGTDWDQSRQLQNKIYKFRGTGKAWDWEVDTENGNYDYLMYADVDMDHPEVIHELRNWGVWYTNTLNLDGFRIDAVKH
SP722   HFDGVDWDQSRQFQNRIYKFRGDGKAWDWEVDSENGNYDYLMYADVDMDHPEVVNELRRWGEWYTNTLNLDGFRIDAVKH
Term    HFDGTDWDESRKLN.RIYKF..QGKAWDWEVSNENGNYDYLMYADIDYDHPDVAAEIKRWGTWYANELQLDGFRLDAVKH
```

FIG 1A

```
              241                                                                          320
707amy  IKYSFTRDWMNHVRSATGKNMFAVAEFWKNDLGAIENYLQKTNWNHSVFDVPLHYNLYNASKSGGNYDMRNIFNGTVVQR
AA-110  IKFSFMRDWLGHVRGQTGKNLFAVAEYWKNDLGALENYLSKTNWTMSAFDVPLHYNLYQASNSSGNYDMRNLFNGTVVQR
AA-16   IQFSFMRNWLGHVRGQTGKNLFAVAEYWKNDLGALENYLSKTNWTMSAFDVPLHYNLYQASNSGGNYDMRNLLNGTLVQR
BAN     IKFSFLRDWVQAVRQATGKEMFTVAEYWQNNAGKLENYLSKTSFNQSVFDVPLHFNLQAASSQGGGYDMRRLLDGTVVSR
BSG     IKFSFFPDWLSYVRSQTGKPLFTVGEYWSYDINKLHNYITKTDGTMSLFDAPLHNKFYTASKSGGAFDMRTLMTNTLMKD
AP1378  IKYSYTRDWLTHVRNTTGKPMFAVAEFWKNDLAAIENYLNKTSWNHSVFDVPLHYNLYNASNSGGYFDMRNILNGSVVQK
SP690   IKYSFTRDWLTHVRNTTGKPMFAVAEFWKNDLGAIENYLNKTSWNHSLFDVPLHYNLYNASNSGGYYDMRNILNGSVVQK
SP722   IKYSFTRDWLTHVRNATGKEMFAVAEFWKNDLGALENYLNKTNWNHSVFDVPLHYNLYNASNSGGNYDMAKLLNGTVVQK
Term    IKFSFLRDWVNHVREKTGKEMFTVAEYWQNDLGALENYLNKTNFNHSVFDVPLHYQFHAASTQGGGYDMRKLLNGTVVSK 321                                                                          400
707amy  HPSHAVTFVDNHDSQPEEALESFVEEWFKPLAYALTLTREQGYPSVFYGDYYGI...PTHGVPAMRSKIDPILEARQKYA
AA-110  HPSHAVTFVDNHDTQPGEALESFVQGWFKPLAYATILTREQGYPQVFYGDYYGI...PSDGVPSYRQQIDPLLKARQQYA
AA-16   HPSHAVTFVDNHDTQPGEALESFVQGWFKPLAYATILTREQGYPQVFYGDYYGI...PSDGVPSYRQQIDPLLKARQQYA
BAN     HPEKAVTFVENHDTQPGQSLESTVQTWFKPLAYAFILTRESGYPQVFYGDMYGTKGTSPKEIPSLKDNIEPILKARKEYA
BSG     QPTLAVTFVDNHDTEPGQALQSWVDPWFKPLAYAFILTRQEGYPCVFYGDYYGI...PQYNIPSLKSKIDPLLIARRDYA
AP1378  HPIHAVTFVDNHDSQPGEALESFVQSWFKPLAYALILTREQGYPSVFYGDYYGI...PTHGVPSMKSKIDPLLQARQTYA
SP690   HPTHAVTFVDNHDSQPGEALESFVQQWFKPLAYALVLTREQGYPSVFYGDYYGI...PTHGVPAMKSKIDPLLQARQTFA
SP722   HPMHAVTFVDNHDSQPGESLESFVQEWFKPLAYALILTREQGYPSVFYGDYYGI...PTHSVPAMKAKIDPLLEARQNFA
Term    HPLKSVTFVDNHDTQPGQSLESTVQTWFKPLAYAFILTRESGYPQVFYGDMYGTKGDSQREIPALKHKIEPILKARKQYA 401                                                                          480
707amy  YGKQNDYLDHHNIIGWTREGNTAHPNSGLATIMSDGAGGSKWMFVGRNKAGQVWSDITGNRTGTVTINADGWGNFSVNGG
AA-110  YGRQHDYFDHWDVIGWTREGNASHPNSGLATIMSDGPGGSKWMYVGRQKAGEVWHDMTGNRSGTVTINQDGWGHFFVNGG
AA-16   YGRQHDYFDHWDVIGWTREGNASHPNSGLATIMSDGPGGSKWMYVGRQKAGEVWHDITGNRSGTVTINQDGWGQFFVNGG
BAN     YGPQHDYIDHPDVIGWTREGDSSAAKSGLAALITDGPGGSKRMYAGLKNAGETWYDITGNRSDTVKIGSDGWGEFHVNDG
BSG     YGTQHDYLDHSDIIGWTREGGTEKPGSGLAALITDGPGGSKWMYVGKQHAGKVFYDLTGNRSDTVTINSDGWGEFKVNGG
AP1378  YGTQHDYFDHHDIIGWTREGDSSHPNSGLATIMSDGPGGNKWMYVGKHKAGQVWRDITGNRSGTVTINADGWGNFTVNGG
SP690   YGTQHDYFDHHDIIGWTREGNSSHPNSGLATIMSDGPGGNKWMYVGKNKAGQVWRDITGNRTGTVTINADGWGNFSVNGG
SP722   YGTQHDYFDHHNIIGWTREGNTTHPNSGLATIMSDGPGGEKWMYVGQNKAGQVWHDITGNKPGTVTINADGWANFSVNGG
Term    YGAQHDYFDHHDIVGWTREGDSSVANSGLAALITDGPGGAKRMYVGRQNAGETWHDITGNRSEPVVINSEGWGEFHVNGG
```

*FIG 1B*

```
              481                                        520
707amy    SVSIWVNK................................
 AA-110   SVSVWVKR................................
  AA-16   SVSVWVKR................................
    BAN   SVSIYVQK................................
    BSG   SVSVWPRKTTVSTIARPITTRPWTGEFVRWTEPRLVAWPI
 AP1378   AVSVWVKQ................................
  SP690   SVSVWVKQ................................
  SP722   SVSIWVKR................................
   Term   SVSIYVQR................................
```

FIG 1C

SEQUENCE LISTING

<160> NUMBER OF SEQ ID NOS: 21

<210> SEQ ID NO 1
<211> LENGTH: 1458
<212> TYPE: DNA
<213> ORGANISM: Bacillus sp.
<220> FEATURE:
<221> NAME/KEY: CDS
<222> LOCATION: (1)..(1458)

<400> SEQUENCE: 1

| cat | cac | gat | ggg | acg | aac | gga | acg | att | atg | caa | tat | ttt | gaa | tgg | aac | 48 |
|---|---|---|---|---|---|---|---|---|---|---|---|---|---|---|---|---|
| His | His | Asp | Gly | Thr | Asn | Gly | Thr | Ile | Met | Gln | Tyr | Phe | Glu | Trp | Asn | |
| 1 | | | | 5 | | | | | 10 | | | | | 15 | | |

| gtt | ccg | aat | gat | gga | caa | cat | tgg | aac | cgc | tta | cac | aac | aat | gct | cag | 96 |
|---|---|---|---|---|---|---|---|---|---|---|---|---|---|---|---|---|
| Val | Pro | Asn | Asp | Gly | Gln | His | Trp | Asn | Arg | Leu | His | Asn | Asn | Ala | Gln | |
| | | | 20 | | | | | 25 | | | | | 30 | | | |

| aat | tta | aaa | aat | gct | gga | att | act | gcg | att | tgg | att | ccc | cct | gca | tgg | 144 |
|---|---|---|---|---|---|---|---|---|---|---|---|---|---|---|---|---|
| Asn | Leu | Lys | Asn | Ala | Gly | Ile | Thr | Ala | Ile | Trp | Ile | Pro | Pro | Ala | Trp | |
| | | 35 | | | | | 40 | | | | | 45 | | | | |

| aaa | gga | acg | agc | caa | aat | gat | gta | ggc | tat | ggt | gcg | tat | gac | ctc | tat | 192 |
|---|---|---|---|---|---|---|---|---|---|---|---|---|---|---|---|---|
| Lys | Gly | Thr | Ser | Gln | Asn | Asp | Val | Gly | Tyr | Gly | Ala | Tyr | Asp | Leu | Tyr | |
| 50 | | | | | 55 | | | | | 60 | | | | | | |

| gac | ctt | ggt | gaa | ttt | aat | caa | aaa | gga | aca | gta | cgt | acg | aaa | tat | ggc | 240 |
|---|---|---|---|---|---|---|---|---|---|---|---|---|---|---|---|---|
| Asp | Leu | Gly | Glu | Phe | Asn | Gln | Lys | Gly | Thr | Val | Arg | Thr | Lys | Tyr | Gly | |
| 65 | | | | | 70 | | | | | 75 | | | | | 80 | |

| aca | aaa | gca | gaa | tta | gaa | cga | gcg | att | cgc | tcg | tta | aaa | gcg | aac | ggg | 288 |
|---|---|---|---|---|---|---|---|---|---|---|---|---|---|---|---|---|
| Thr | Lys | Ala | Glu | Leu | Glu | Arg | Ala | Ile | Arg | Ser | Leu | Lys | Ala | Asn | Gly | |
| | | | | 85 | | | | | 90 | | | | | 95 | | |

| att | caa | gtg | tac | ggt | gat | gtc | gtc | atg | aac | cat | aaa | ggt | ggt | gct | gat | 336 |
|---|---|---|---|---|---|---|---|---|---|---|---|---|---|---|---|---|
| Ile | Gln | Val | Tyr | Gly | Asp | Val | Val | Met | Asn | His | Lys | Gly | Gly | Ala | Asp | |
| | | | 100 | | | | | 105 | | | | | 110 | | | |

| ttt | acc | gag | cga | gtt | caa | gcg | gtt | gaa | gta | aat | ccg | caa | aat | cga | aat | 384 |
|---|---|---|---|---|---|---|---|---|---|---|---|---|---|---|---|---|
| Phe | Thr | Glu | Arg | Val | Gln | Ala | Val | Glu | Val | Asn | Pro | Gln | Asn | Arg | Asn | |
| | | 115 | | | | | 120 | | | | | 125 | | | | |

| caa | gaa | gtg | tct | ggc | act | tat | gaa | atc | gaa | gca | tgg | act | gga | ttt | aat | 432 |
|---|---|---|---|---|---|---|---|---|---|---|---|---|---|---|---|---|
| Gln | Glu | Val | Ser | Gly | Thr | Tyr | Glu | Ile | Glu | Ala | Trp | Thr | Gly | Phe | Asn | |
| | 130 | | | | | 135 | | | | | 140 | | | | | |

| ttc | cct | gga | cgt | ggc | aat | caa | cac | tct | tcg | ttt | aaa | tgg | cgt | tgg | tac | 480 |
|---|---|---|---|---|---|---|---|---|---|---|---|---|---|---|---|---|
| Phe | Pro | Gly | Arg | Gly | Asn | Gln | His | Ser | Ser | Phe | Lys | Trp | Arg | Trp | Tyr | |
| 145 | | | | | 150 | | | | | 155 | | | | | 160 | |

| cat | ttt | gat | gga | acg | gac | tgg | gat | caa | tct | cgt | caa | ctc | tca | aat | cgt | 528 |
|---|---|---|---|---|---|---|---|---|---|---|---|---|---|---|---|---|
| His | Phe | Asp | Gly | Thr | Asp | Trp | Asp | Gln | Ser | Arg | Gln | Leu | Ser | Asn | Arg | |
| | | | | 165 | | | | | 170 | | | | | 175 | | |

| atc | tat | aaa | ttt | aga | gga | gac | ggg | aaa | gca | tgg | gac | tgg | gaa | gta | gac | 576 |
|---|---|---|---|---|---|---|---|---|---|---|---|---|---|---|---|---|
| Ile | Tyr | Lys | Phe | Arg | Gly | Asp | Gly | Lys | Ala | Trp | Asp | Trp | Glu | Val | Asp | |
| | | | 180 | | | | | 185 | | | | | 190 | | | |

| act | gaa | aac | gga | aac | tac | gat | tac | tta | atg | tat | gca | gac | gtt | gac | atg | 624 |
|---|---|---|---|---|---|---|---|---|---|---|---|---|---|---|---|---|
| Thr | Glu | Asn | Gly | Asn | Tyr | Asp | Tyr | Leu | Met | Tyr | Ala | Asp | Val | Asp | Met | |
| | | 195 | | | | | 200 | | | | | 205 | | | | |

| aac | cat | cct | gaa | gtc | ata | aac | gaa | tta | aac | cga | tgg | ggc | gta | tgg | tac | 672 |
|---|---|---|---|---|---|---|---|---|---|---|---|---|---|---|---|---|
| Asn | His | Pro | Glu | Val | Ile | Asn | Glu | Leu | Asn | Arg | Trp | Gly | Val | Trp | Tyr | |
| | 210 | | | | | 215 | | | | | 220 | | | | | |

| gca | aat | acc | ctt | aat | tta | gac | ggc | ttt | aga | ctt | gat | gcg | gtg | aag | cat | 720 |
|---|---|---|---|---|---|---|---|---|---|---|---|---|---|---|---|---|
| Ala | Asn | Thr | Leu | Asn | Leu | Asp | Gly | Phe | Arg | Leu | Asp | Ala | Val | Lys | His | |
| 225 | | | | | 230 | | | | | 235 | | | | | 240 | |

| att | caa | ttc | agc | ttc | atg | cgc | aac | tgg | ctc | gga | cat | gtt | cga | gga | caa | 768 |
|---|---|---|---|---|---|---|---|---|---|---|---|---|---|---|---|---|
| Ile | Gln | Phe | Ser | Phe | Met | Arg | Asn | Trp | Leu | Gly | His | Val | Arg | Gly | Gln |  |
| | | | | 245 | | | | | 250 | | | | | 255 | | |

-continued

| | | |
|---|---|---|
| aca ggc aag aac ctc ttt gca gtt gca gaa tat tgg aaa aac gac tta<br>Thr Gly Lys Asn Leu Phe Ala Val Ala Glu Tyr Trp Lys Asn Asp Leu<br>260                  265                  270 | 816 | |
| ggt gcc cta gaa aat tat tta agt aaa aca aat tgg acg atg agc gcc<br>Gly Ala Leu Glu Asn Tyr Leu Ser Lys Thr Asn Trp Thr Met Ser Ala<br>275                  280                  285 | 864 | |
| ttt gat gtg cct ctt cat tac aac ctt tac caa gcg tca aat agc ggc<br>Phe Asp Val Pro Leu His Tyr Asn Leu Tyr Gln Ala Ser Asn Ser Gly<br>290                  295                  300 | 912 | |
| gga aat tac gac atg aga aat ttg tta aat gga acg ctc gtt cag cgt<br>Gly Asn Tyr Asp Met Arg Asn Leu Leu Asn Gly Thr Leu Val Gln Arg<br>305                  310                  315                  320 | 960 | |
| cac cct agt cat gca gtg acg ttc gtc gat aac cat gac aca cag cct<br>His Pro Ser His Ala Val Thr Phe Val Asp Asn His Asp Thr Gln Pro<br>325                  330                  335 | 1008 | |
| gga gaa gct ctt gag tcg ttc gtc caa ggc tgg ttt aaa ccg ctc gct<br>Gly Glu Ala Leu Glu Ser Phe Val Gln Gly Trp Phe Lys Pro Leu Ala<br>340                  345                  350 | 1056 | |
| tat gca acg att ctt acg aga gaa caa ggc tac cca caa gtg ttt tac<br>Tyr Ala Thr Ile Leu Thr Arg Glu Gln Gly Tyr Pro Gln Val Phe Tyr<br>355                  360                  365 | 1104 | |
| ggc gat tat tat ggt att ccg agt gat ggc gtt cca agc tat cgt caa<br>Gly Asp Tyr Tyr Gly Ile Pro Ser Asp Gly Val Pro Ser Tyr Arg Gln<br>370                  375                  380 | 1152 | |
| caa att gat cca ctt tta aaa gcc cgt cag caa tat gct tat gga aga<br>Gln Ile Asp Pro Leu Leu Lys Ala Arg Gln Gln Tyr Ala Tyr Gly Arg<br>385                  390                  395                  400 | 1200 | |
| cag cac gat tac ttc gat cat tgg gat gta att ggc tgg acg cgt gaa<br>Gln His Asp Tyr Phe Asp His Trp Asp Val Ile Gly Trp Thr Arg Glu<br>405                  410                  415 | 1248 | |
| ggg aac gcg tct cac ccg aat tct ggg ctt gcg acc ata atg tcc gat<br>Gly Asn Ala Ser His Pro Asn Ser Gly Leu Ala Thr Ile Met Ser Asp<br>420                  425                  430 | 1296 | |
| ggt cca ggt gga tcg aaa tgg atg tat gtt ggt cgt caa aaa gct ggt<br>Gly Pro Gly Gly Ser Lys Trp Met Tyr Val Gly Arg Gln Lys Ala Gly<br>435                  440                  445 | 1344 | |
| gaa gta tgg cat gac ata act gga aac cgc agc ggc act gtg aca att<br>Glu Val Trp His Asp Ile Thr Gly Asn Arg Ser Gly Thr Val Thr Ile<br>450                  455                  460 | 1392 | |
| aac cag gac ggc tgg gga caa ttt ttt gtc aac ggt ggt tcc gtc tcc<br>Asn Gln Asp Gly Trp Gly Gln Phe Phe Val Asn Gly Gly Ser Val Ser<br>465                  470                  475                  480 | 1440 | |
| gta tgg gtg aaa cga taa<br>Val Trp Val Lys Arg<br>485 | 1458 | |

<210> SEQ ID NO 2
<211> LENGTH: 485
<212> TYPE: PRT
<213> ORGANISM: Bacillus sp.

<400> SEQUENCE: 2

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
                20                  25                  30

Asn Leu Lys Asn Ala Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

```
Asp Leu Gly Glu Phe Asn Gln Lys Gly Thr Val Arg Thr Lys Tyr Gly
 65                  70                  75                  80

Thr Lys Ala Glu Leu Glu Arg Ala Ile Arg Ser Leu Lys Ala Asn Gly
             85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
            115                 120                 125

Gln Glu Val Ser Gly Thr Tyr Glu Ile Glu Ala Trp Thr Gly Phe Asn
130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ser Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
            195                 200                 205

Asn His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Gln Phe Ser Phe Met Arg Asn Trp Leu His Val Arg Gly Gln
            245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
            275                 280                 285

Phe Asp Val Pro Leu His Tyr Asn Leu Tyr Gln Ala Ser Asn Ser Gly
            290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
            355                 360                 365

Gly Asp Tyr Tyr Gly Ile Pro Ser Asp Gly Val Pro Ser Tyr Arg Gln
370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
            435                 440                 445

Glu Val Trp His Asp Ile Thr Gly Asn Arg Ser Gly Thr Val Thr Ile
450                 455                 460
```

-continued

```
Asn Gln Asp Gly Trp Gly Gln Phe Phe Val Asn Gly Gly Ser Val Ser
465                 470                 475                 480

Val Trp Val Lys Arg
            485
```

<210> SEQ ID NO 3
<211> LENGTH: 1458
<212> TYPE: DNA
<213> ORGANISM: Bacillus sp.
<220> FEATURE:
<221> NAME/KEY: CDS
<222> LOCATION: (1)..(1458)

<400> SEQUENCE: 3

```
cat cac gat ggg acg aac gga acg att atg cag tat ttt gaa tgg aac      48
His His Asp Gly Thr Asn Gly Thr Ile Met Gln Tyr Phe Glu Trp Asn
1               5                  10                  15 gtt ccg aat gat gga caa cat tgg aac cgc tta cac aac aac gct caa      96
Val Pro Asn Asp Gly Gln His Trp Asn Arg Leu His Asn Asn Ala Gln
            20                  25                  30 aat tta aaa aat gcc gga att aca gca atc tgg att cca cct gcg tgg    144
Asn Leu Lys Asn Ala Gly Ile Thr Ala Ile Trp Ile Pro Pro Ala Trp
        35                  40                  45 aaa gga acg agc caa aat gat gta ggc tac ggt gcg tat gac ctt tat    192
Lys Gly Thr Ser Gln Asn Asp Val Gly Tyr Gly Ala Tyr Asp Leu Tyr
    50                  55                  60 gac ctt ggt gaa ttt aac caa aaa gga acg gtc cgt acg aaa tat gga    240
Asp Leu Gly Glu Phe Asn Gln Lys Gly Thr Val Arg Thr Lys Tyr Gly
65                  70                  75                  80 aca aaa gca gaa tta gaa cga gcg att cgt tcg tta aag gcg aac ggg    288
Thr Lys Ala Glu Leu Glu Arg Ala Ile Arg Ser Leu Lys Ala Asn Gly
                85                  90                  95 att caa gtg tat ggc gat gtt gtt atg aac cat aaa ggc gga gct gat    336
Ile Gln Val Tyr Gly Asp Val Val Met Asn His Lys Gly Gly Ala Asp
            100                 105                 110 ttc acc gag cgt gtt caa gcg gtt gaa gtg aac ccg caa aac cga aac    384
Phe Thr Glu Arg Val Gln Ala Val Glu Val Asn Pro Gln Asn Arg Asn
        115                 120                 125 caa gaa gtg tct ggc act tat caa atc gaa gca tgg aca ggg ttc aat    432
Gln Glu Val Ser Gly Thr Tyr Gln Ile Glu Ala Trp Thr Gly Phe Asn
    130                 135                 140 ttt cct gga cgt ggc aat caa cat tct tcg ttt aaa tgg cgc tgg tat    480
Phe Pro Gly Arg Gly Asn Gln His Ser Ser Phe Lys Trp Arg Trp Tyr
145                 150                 155                 160 cat ttc gat ggg acg gat tgg gac cag tct cgc caa ctc gca aat cgt    528
His Phe Asp Gly Thr Asp Trp Asp Gln Ser Arg Gln Leu Ala Asn Arg
                165                 170                 175 att tat aag ttt aga gga gac gga aaa gca tgg gac tgg gaa gtt gac    576
Ile Tyr Lys Phe Arg Gly Asp Gly Lys Ala Trp Asp Trp Glu Val Asp
            180                 185                 190 act gaa aat ggg aac tat gat tac tta atg tat gca gac gtt gac atg    624
Thr Glu Asn Gly Asn Tyr Asp Tyr Leu Met Tyr Ala Asp Val Asp Met
        195                 200                 205 gat cat cca gaa gtg att aac gaa cta aac cgt tgg ggc gtc tgg tac    672
Asp His Pro Glu Val Ile Asn Glu Leu Asn Arg Trp Gly Val Trp Tyr
    210                 215                 220 gcg aat acc ctt aat tta gac ggc ttc cga ctg gat gca gtg aaa cat    720
Ala Asn Thr Leu Asn Leu Asp Gly Phe Arg Leu Asp Ala Val Lys His
225                 230                 235                 240
```

```
att aaa ttt agc ttc atg cgt gat tgg tta ggg cat gtt cgc ggg caa        768
Ile Lys Phe Ser Phe Met Arg Asp Trp Leu Gly His Val Arg Gly Gln
            245                 250                 255 acg ggc aag aat ctt ttt gcc gtt gca gag tat tgg aag aat gac cta        816
Thr Gly Lys Asn Leu Phe Ala Val Ala Glu Tyr Trp Lys Asn Asp Leu
        260                 265                 270 ggg gct tta gaa aat tat tta agc aaa aca aat tgg acg atg agc gcc        864
Gly Ala Leu Glu Asn Tyr Leu Ser Lys Thr Asn Trp Thr Met Ser Ala
    275                 280                 285 ttt gat gtt ccg ctt cat tac aac ctt tat caa gcg tca aat agt agc        912
Phe Asp Val Pro Leu His Tyr Asn Leu Tyr Gln Ala Ser Asn Ser Ser
290                 295                 300 gga aat tac gac atg aga aac ttg tta aat gga aca ctc gtt caa cgt        960
Gly Asn Tyr Asp Met Arg Asn Leu Leu Asn Gly Thr Leu Val Gln Arg
305                 310                 315                 320 cat ccg agc cat gcg gtt acg ttt gtc gat aac cac gac aca cag cct       1008
His Pro Ser His Ala Val Thr Phe Val Asp Asn His Asp Thr Gln Pro
            325                 330                 335 gga gaa gcc ctc gaa tcg ttc gtt caa ggc tgg ttt aaa cca cta gct       1056
Gly Glu Ala Leu Glu Ser Phe Val Gln Gly Trp Phe Lys Pro Leu Ala
        340                 345                 350 tat gca acg att ctt acg aga gag caa ggc tac cca caa gtg ttt tac       1104
Tyr Ala Thr Ile Leu Thr Arg Glu Gln Gly Tyr Pro Gln Val Phe Tyr
    355                 360                 365 ggc gat tat tat ggc atc cca agt gac ggt gtt cca agc tac cgt caa       1152
Gly Asp Tyr Tyr Gly Ile Pro Ser Asp Gly Val Pro Ser Tyr Arg Gln
370                 375                 380 cag atc gac cca ctt tta aaa gct cgt caa caa tat gct tat ggt aga       1200
Gln Ile Asp Pro Leu Leu Lys Ala Arg Gln Gln Tyr Ala Tyr Gly Arg
385                 390                 395                 400 cag cac gat tac ttt gat cat tgg gat gta att ggc tgg aca cgt gaa       1248
Gln His Asp Tyr Phe Asp His Trp Asp Val Ile Gly Trp Thr Arg Glu
            405                 410                 415 gga aac gca tct cac ccg aac tca gga ctt gca acc att atg tct gat       1296
Gly Asn Ala Ser His Pro Asn Ser Gly Leu Ala Thr Ile Met Ser Asp
        420                 425                 430 ggt cca ggt gga tca aaa tgg atg tat gtt ggc cgt cag aaa gct ggc       1344
Gly Pro Gly Gly Ser Lys Trp Met Tyr Val Gly Arg Gln Lys Ala Gly
    435                 440                 445 gaa gtg tgg cat gac atg act gga aac cgc agt ggc act gtg aca att       1392
Glu Val Trp His Asp Met Thr Gly Asn Arg Ser Gly Thr Val Thr Ile
450                 455                 460 aat caa gac ggc tgg gga cac ttt ttt gtc aac ggc ggc tct gtc tcc       1440
Asn Gln Asp Gly Trp Gly His Phe Phe Val Asn Gly Gly Ser Val Ser
465                 470                 475                 480 gta tgg gtg aaa cga taa                                                1458
Val Trp Val Lys Arg
            485

<210> SEQ ID NO 4
<211> LENGTH: 485
<212> TYPE: PRT
<213> ORGANISM: Bacillus sp.

<400> SEQUENCE: 4

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30
```

-continued

```
Asn Leu Lys Asn Ala Gly Ile Thr Ala Ile Trp Ile Pro Pro Ala Trp
         35                  40                  45
Lys Gly Thr Ser Gln Asn Asp Val Gly Tyr Gly Ala Tyr Asp Leu Tyr
     50                  55                  60
Asp Leu Gly Glu Phe Asn Gln Lys Gly Thr Val Arg Thr Lys Tyr Gly
 65                  70                  75                  80
Thr Lys Ala Glu Leu Glu Arg Ala Ile Arg Ser Leu Lys Ala Asn Gly
                 85                  90                  95
Ile Gln Val Tyr Gly Asp Val Val Met Asn His Lys Gly Gly Ala Asp
             100                 105                 110
Phe Thr Glu Arg Val Gln Ala Val Glu Val Asn Pro Gln Asn Arg Asn
         115                 120                 125
Gln Glu Val Ser Gly Thr Tyr Gln Ile Glu Ala Trp Thr Gly Phe Asn
     130                 135                 140
Phe Pro Gly Arg Gly Asn Gln His Ser Ser Phe Lys Trp Arg Trp Tyr
145                 150                 155                 160
His Phe Asp Gly Thr Asp Trp Asp Gln Ser Arg Gln Leu Ala Asn Arg
                 165                 170                 175
Ile Tyr Lys Phe Arg Gly Asp Gly Lys Ala Trp Asp Trp Glu Val Asp
             180                 185                 190
Thr Glu Asn Gly Asn Tyr Asp Tyr Leu Met Tyr Ala Asp Val Asp Met
         195                 200                 205
Asp His Pro Glu Val Ile Asn Glu Leu Asn Arg Trp Gly Val Trp Tyr
210                 215                 220
Ala Asn Thr Leu Asn Leu Asp Gly Phe Arg Leu Asp Ala Val Lys His
225                 230                 235                 240
Ile Lys Phe Ser Phe Met Arg Asp Trp Leu Gly His Val Arg Gly Gln
             245                 250                 255
Thr Gly Lys Asn Leu Phe Ala Val Ala Glu Tyr Trp Lys Asn Asp Leu
         260                 265                 270
Gly Ala Leu Glu Asn Tyr Leu Ser Lys Thr Asn Trp Thr Met Ser Ala
     275                 280                 285
Phe Asp Val Pro Leu His Tyr Asn Leu Tyr Gln Ala Ser Asn Ser Ser
 290                 295                 300
Gly Asn Tyr Asp Met Arg Asn Leu Leu Asn Gly Thr Leu Val Gln Arg
305                 310                 315                 320
His Pro Ser His Ala Val Thr Phe Val Asp Asn His Asp Thr Gln Pro
                 325                 330                 335
Gly Glu Ala Leu Glu Ser Phe Val Gln Gly Trp Phe Lys Pro Leu Ala
             340                 345                 350
Tyr Ala Thr Ile Leu Thr Arg Glu Gln Gly Tyr Pro Gln Val Phe Tyr
         355                 360                 365
Gly Asp Tyr Tyr Gly Ile Pro Ser Asp Gly Val Pro Ser Tyr Arg Gln
     370                 375                 380
Gln Ile Asp Pro Leu Leu Lys Ala Arg Gln Gln Tyr Ala Tyr Gly Arg
385                 390                 395                 400
Gln His Asp Tyr Phe Asp His Trp Asp Val Ile Gly Trp Thr Arg Glu
                 405                 410                 415
Gly Asn Ala Ser His Pro Asn Ser Gly Leu Ala Thr Ile Met Ser Asp
             420                 425                 430
Gly Pro Gly Gly Ser Lys Trp Met Tyr Val Gly Arg Gln Lys Ala Gly
         435                 440                 445
```

```
Glu Val Trp His Asp Met Thr Gly Asn Arg Ser Gly Thr Val Thr Ile
    450                 455                 460
Asn Gln Asp Gly Trp Gly His Phe Phe Val Asn Gly Ser Val Ser
465                 470                 475                 480
Val Trp Val Lys Arg
                485

<210> SEQ ID NO 5
<211> LENGTH: 7
<212> TYPE: PRT
<213> ORGANISM: unknown
<220> FEATURE:
<223> OTHER INFORMATION: Conserved regions in known Bacillus alpha
      amylase
<221> NAME/KEY: misc_feature
<223> OTHER INFORMATION: Xaa in position 5=L, V, I
<221> NAME/KEY: misc_feature
<223> OTHER INFORMATION: Xaa in position 7=I, L

<400> SEQUENCE: 5

Gly Ile Thr Ala Xaa Trp Xaa
1               5

<210> SEQ ID NO 6
<211> LENGTH: 9
<212> TYPE: PRT
<213> ORGANISM: unknown
<220> FEATURE:
<223> OTHER INFORMATION: Conserved regions in known Bacillus alpha
      amylases.
<221> NAME/KEY: misc_feature
<223> OTHER INFORMATION: Xaa in position 3=G, A
<221> NAME/KEY: misc_feature
<223> OTHER INFORMATION: Xaa in position 5=V, F, L
<221> NAME/KEY: misc_feature
<223> OTHER INFORMATION: Xaa in position 7=M, L, I, F

<400> SEQUENCE: 6

Val Tyr Xaa Asp Xaa Val Xaa Asn His
1               5

<210> SEQ ID NO 7
<211> LENGTH: 10
<212> TYPE: PRT
<213> ORGANISM: unknown
<220> FEATURE:
<223> OTHER INFORMATION: Conserved regions in known Bacillus alpha
      amylases.
<221> NAME/KEY: misc_feature
<223> OTHER INFORMATION: Xaa in position 3=F, I
<221> NAME/KEY: misc_feature
<223> OTHER INFORMATION: Xaa in position 5=F, L, I, V
<221> NAME/KEY: misc_feature
<223> OTHER INFORMATION: Xaa in position 8=A, V

<400> SEQUENCE: 7

Asp Gly Xaa Arg Xaa Asp Ala Xaa Lys His
1               5                   10

<210> SEQ ID NO 8
<211> LENGTH: 10
<212> TYPE: PRT
<213> ORGANISM: Unknown
<220> FEATURE:
<223> OTHER INFORMATION: Conserved regions in known Bacillus
      alpha-amylases.
<221> NAME/KEY: misc_feature
<223> OTHER INFORMATION: Xaa in position 3=F, I
<221> NAME/KEY: misc_feature
<223> OTHER INFORMATION: Xaa in position 5=F, L, I, V
```

<221> NAME/KEY: misc_feature
<223> OTHER INFORMATION: Xaa in position 8=A, V

<400> SEQUENCE: 8

Asp Gly Xaa Arg Xaa Asp Ala Xaa Lys His
1               5                  10

<210> SEQ ID NO 9
<211> LENGTH: 8
<212> TYPE: PRT
<213> ORGANISM: unknown
<220> FEATURE:
<223> OTHER INFORMATION: Conserved regions in known Bacillus
      alpha-amylase.
<221> NAME/KEY: misc_feature
<223> OTHER INFORMATION: Xaa=D, E

<400> SEQUENCE: 9

Val Thr Phe Val Xaa Asn His Asp
1               5

<210> SEQ ID NO 10
<211> LENGTH: 6
<212> TYPE: PRT
<213> ORGANISM: Unknown
<220> FEATURE:
<223> OTHER INFORMATION: Conserved regions in known Bacillus alpha
      amylases.

<400> SEQUENCE: 10

Gly Trp Thr Arg Glu Gly
1               5

<210> SEQ ID NO 11
<211> LENGTH: 47
<212> TYPE: DNA
<213> ORGANISM: Artificial Sequence
<220> FEATURE:
<221> NAME/KEY: misc_feature
<223> OTHER INFORMATION: Primer 197cloningC

<400> SEQUENCE: 11
ccgagctcgg ccggctgggc cgtcgactta tcgtttcacc catacgg                    47

<210> SEQ ID NO 12
<211> LENGTH: 38
<212> TYPE: DNA
<213> ORGANISM: Artificial Sequence
<220> FEATURE:
<221> NAME/KEY: misc_feature
<223> OTHER INFORMATION: Primer 197cloningN

<400> SEQUENCE: 12
cattctgcag cagcggcgca tcacgatggg acgaacgg                              38

<210> SEQ ID NO 13
<211> LENGTH: 485
<212> TYPE: PRT
<213> ORGANISM: Bacillus

<400> SEQUENCE: 13

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

-continued

```
Asn Leu Lys Ser Lys Gly Ile Thr Ala Val Trp Ile Pro Pro Ala Trp
     35                  40                  45

Lys Gly Ala Ser Gln Asn Asp Val Gly Tyr Gly Ala Tyr Asp Leu Tyr
     50                  55                  60

Asp Leu Gly Glu Phe Asn Gln Lys Gly Thr Val Arg Thr Lys Tyr Gly
 65                  70                  75                  80

Thr Arg Ser Gln Leu Gln Ala Ala Val Thr Ser Leu Lys Asn Asn Gly
                 85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
             115                 120                 125

Gln Glu Val Thr Gly Glu Tyr Thr Ile Glu Ala Trp Thr Arg Phe Asp
     130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                 165                 170                 175

Ile Tyr Lys Phe Arg Gly His Gly Lys Ala Trp Asp Trp Glu Val Asp
             180                 185                 190

Thr Glu Asn Gly Asn Tyr Asp Tyr Leu Met Tyr Ala Asp Ile Asp Met
     195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                 245                 250                 255

Thr Gly Lys Asn Met Phe Ala Val Ala Glu Phe Trp Lys Asn Asp Leu
             260                 265                 270

Gly Ala Ile Glu Asn Tyr Leu Gln Lys Thr Asn Trp Asn His Ser Val
     275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                 325                 330                 335

Glu Glu Ala Leu Glu Ser Phe Val Glu Glu Trp Phe Lys Pro Leu Ala
             340                 345                 350

Tyr Ala Leu Thr Leu Thr Arg Glu Gln Gly Tyr Pro Ser Val Phe Tyr
     355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                 405                 410                 415

Gly Asn Thr Ala His Pro Asn Ser Gly Leu Ala Thr Ile Met Ser Asp
             420                 425                 430

Gly Ala Gly Gly Ser Lys Trp Met Phe Val Gly Arg Asn Lys Ala Gly
     435                 440                 445
```

-continued

```
Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 14
<211> LENGTH: 485
<212> TYPE: PRT
<213> ORGANISM: Bacillus

<400> SEQUENCE: 14

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
                20                  25                  30

Asn Leu Lys Asn Ala Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335
```

-continued

```
Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
        435                 440                 445

Glu Val Trp His Asp Met Thr Gly Asn Arg Ser Gly Thr Val Thr Ile
    450                 455                 460

Asn Gln Asp Gly Trp Gly His Phe Phe Val Asn Gly Gly Ser Val Ser
465                 470                 475                 480

Val Trp Val Lys Arg
                485

<210> SEQ ID NO 15
<211> LENGTH: 485
<212> TYPE: PRT
<213> ORGANISM: Bacillus

<400> SEQUENCE: 15

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Glu Ile Glu Ala Trp Thr Gly Phe Asn
130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ser Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asn His Pro Glu Val Ile Asn Glu Leu Asn Arg Trp Gly Val Trp Tyr
210                 215                 220
```

```
Ala Asn Thr Leu Asn Leu Asp Gly Phe Arg Leu Asp Ala Val Lys His
225                 230                 235                 240

Ile Gln Phe Ser Phe Met Arg Asn Trp Leu Gly His Val Arg Gly Gln
            245                 250                 255

Thr Gly Lys Asn Leu Phe Ala Val Ala Glu Tyr Trp Lys Asn Asp Leu
        260                 265                 270

Gly Ala Leu Glu Asn Tyr Leu Ser Lys Thr Asn Trp Thr Met Ser Ala
    275                 280                 285

Phe Asp Val Pro Leu His Tyr Asn Leu Tyr Gln Ala Ser Asn Ser Gly
290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
        435                 440                 445

Glu Val Trp His Asp Ile Thr Gly Asn Arg Ser Gly Thr Val Thr Ile
    450                 455                 460

Asn Gln Asp Gly Trp Gly Gln Phe Phe Val Asn Gly Gly Ser Val Ser
465                 470                 475                 480

Val Trp Val Lys Arg
                485

<210> SEQ ID NO 16
<211> LENGTH: 483
<212> TYPE: PRT
<213> ORGANISM: Bacillus

<400> SEQUENCE: 16

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110
```

-continued

```
Val Thr Ala Val Glu Val Asn Pro Ala Asn Arg Asn Gln Glu Thr Ser
            115                 120                 125
Glu Glu Tyr Gln Ile Lys Ala Trp Thr Asp Phe Arg Phe Pro Gly Arg
    130                 135                 140
Gly Asn Thr Tyr Ser Asp Phe Lys Trp His Trp Tyr His Phe Asp Gly
145                 150                 155                 160
Ala Asp Trp Asp Glu Ser Arg Lys Ile Ser Arg Ile Phe Lys Phe Arg
                165                 170                 175
Gly Glu Gly Lys Ala Trp Asp Trp Glu Val Ser Ser Glu Asn Gly Asn
                180                 185                 190
Tyr Asp Tyr Leu Met Tyr Ala Asp Val Asp Tyr Asp His Pro Asp Val
            195                 200                 205
Val Ala Glu Thr Lys Lys Trp Gly Ile Trp Tyr Ala Asn Glu Leu Ser
    210                 215                 220
Leu Asp Gly Phe Arg Ile Asp Ala Ala Lys His Ile Lys Phe Ser Phe
225                 230                 235                 240
Leu Arg Asp Trp Val Gln Ala Val Arg Gln Ala Thr Gly Lys Glu Met
                245                 250                 255
Phe Thr Val Ala Glu Tyr Trp Gln Asn Asn Ala Gly Lys Leu Glu Asn
            260                 265                 270
Tyr Leu Asn Lys Thr Ser Phe Asn Gln Ser Val Phe Asp Val Pro Leu
        275                 280                 285
His Phe Asn Leu Gln Ala Ala Ser Ser Gln Gly Gly Gly Tyr Asp Met
    290                 295                 300
Arg Arg Leu Leu Asp Gly Thr Val Val Ser Arg His Pro Glu Lys Ala
305                 310                 315                 320
Val Thr Phe Val Glu Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Thr Ser Pro Lys Glu Ile Pro Ser Leu Lys Asp Asn Ile
    370                 375                 380
Glu Pro Ile Leu Lys Ala Arg Lys Glu Tyr Ala Tyr Gly Pro Gln His
385                 390                 395                 400
Asp Tyr Ile Asp His Pro Asp Val Ile Gly Trp Thr Arg Glu Gly Asp
                405                 410                 415
Ser Ser Ala Ala Lys Ser Gly Leu Ala Ala Leu Ile Thr Asp Gly Pro
            420                 425                 430
Gly Gly Ser Lys Arg Met Tyr Ala Gly Leu Lys Asn Ala Gly Glu Thr
        435                 440                 445
Trp Tyr Asp Ile Thr Gly Asn Arg Ser Asp Thr Val Lys Ile Gly Ser
    450                 455                 460
Asp Gly Trp Gly Glu Phe His Val Asn Asp Gly Ser Val Ser Ile Tyr
465                 470                 475                 480
Val Gln Lys
```

```
<210> SEQ ID NO 17
<211> LENGTH: 515
<212> TYPE: PRT
<213> ORGANISM: Bacillus

<400> SEQUENCE: 17
```

| | | | | | | | | | | | | | | |
|---|---|---|---|---|---|---|---|---|---|---|---|---|---|---|
| Ala | Ala | Pro | Phe | Asn | Gly | Thr | Met | Met | Gln | Tyr | Phe | Glu | Trp | Tyr | Leu |
| 1 | | | | 5 | | | | | 10 | | | | | 15 | |
| Pro | Asp | Asp | Gly | Thr | Leu | Trp | Thr | Lys | Val | Ala | Asn | Glu | Ala | Asn | Asn |
| | | | 20 | | | | | 25 | | | | | 30 | | |
| Leu | Ser | Ser | Leu | Gly | Ile | Thr | Ala | Leu | Trp | Leu | Pro | Pro | Ala | Tyr | Lys |
| | | 35 | | | | | 40 | | | | | 45 | | | |
| Gly | Thr | Ser | Arg | Ser | Asp | Val | Gly | Tyr | Gly | Val | Tyr | Asp | Leu | Tyr | Asp |
| | 50 | | | | | 55 | | | | | 60 | | | | |
| Leu | Gly | Glu | Phe | Asn | Gln | Lys | Gly | Thr | Val | Arg | Thr | Lys | Tyr | Gly | Thr |
| 65 | | | | | 70 | | | | | 75 | | | | | 80 |
| Lys | Ala | Gln | Tyr | Leu | Gln | Ala | Ile | Gln | Ala | Ala | His | Ala | Ala | Gly | Met |
| | | | | 85 | | | | | 90 | | | | | 95 | |
| Gln | Val | Tyr | Ala | Asp | Val | Val | Phe | Asp | His | Lys | Gly | Gly | Ala | Asp | Gly |
| | | | 100 | | | | | 105 | | | | | 110 | | |
| Thr | Glu | Trp | Val | Asp | Ala | Val | Glu | Val | Asn | Pro | Ser | Asp | Arg | Asn | Gln |
| | | 115 | | | | | 120 | | | | | 125 | | | |
| Glu | Ile | Ser | Gly | Thr | Tyr | Gln | Ile | Gln | Ala | Trp | Thr | Lys | Phe | Asp | Phe |
| | 130 | | | | | 135 | | | | | 140 | | | | |
| Pro | Gly | Arg | Gly | Asn | Thr | Tyr | Ser | Ser | Phe | Lys | Trp | Arg | Trp | Tyr | His |
| 145 | | | | | 150 | | | | | 155 | | | | | 160 |
| Phe | Asp | Gly | Val | Asp | Trp | Asp | Glu | Ser | Arg | Lys | Leu | Ser | Arg | Ile | Tyr |
| | | | | 165 | | | | | 170 | | | | | 175 | |
| Lys | Phe | Arg | Gly | Ile | Gly | Lys | Ala | Trp | Asp | Trp | Glu | Val | Asp | Thr | Glu |
| | | | 180 | | | | | 185 | | | | | 190 | | |
| Asn | Gly | Asn | Tyr | Asp | Tyr | Leu | Met | Tyr | Ala | Asp | Leu | Asp | Met | Asp | His |
| | | 195 | | | | | 200 | | | | | 205 | | | |
| Pro | Glu | Val | Val | Thr | Glu | Leu | Lys | Asn | Trp | Gly | Lys | Trp | Tyr | Val | Asn |
| | 210 | | | | | 215 | | | | | 220 | | | | |
| Thr | Thr | Asn | Ile | Asp | Gly | Phe | Arg | Leu | Asp | Ala | Val | Lys | His | Ile | Lys |
| 225 | | | | | 230 | | | | | 235 | | | | | 240 |
| Phe | Ser | Phe | Phe | Pro | Asp | Trp | Leu | Ser | Tyr | Val | Arg | Ser | Gln | Thr | Gly |
| | | | | 245 | | | | | 250 | | | | | 255 | |
| Lys | Pro | Leu | Phe | Thr | Val | Gly | Glu | Tyr | Trp | Ser | Tyr | Asp | Ile | Asn | Lys |
| | | | 260 | | | | | 265 | | | | | 270 | | |
| Leu | His | Asn | Tyr | Ile | Thr | Lys | Thr | Asp | Gly | Thr | Met | Ser | Leu | Phe | Asp |
| | | 275 | | | | | 280 | | | | | 285 | | | |
| Ala | Pro | Leu | His | Asn | Lys | Phe | Tyr | Thr | Ala | Ser | Lys | Ser | Gly | Gly | Ala |
| | 290 | | | | | 295 | | | | | 300 | | | | |
| Phe | Asp | Met | Arg | Thr | Leu | Met | Thr | Asn | Thr | Leu | Met | Lys | Asp | Gln | Pro |
| 305 | | | | | 310 | | | | | 315 | | | | | 320 |
| Thr | Leu | Ala | Val | Thr | Phe | Val | Asp | Asn | His | Asp | Thr | Glu | Pro | Gly | Gln |
| | | | | 325 | | | | | 330 | | | | | 335 | |
| Ala | Leu | Gln | Ser | Trp | Val | Asp | Pro | Trp | Phe | Lys | Pro | Leu | Ala | Tyr | Ala |
| | | | 340 | | | | | 345 | | | | | 350 | | |
| Phe | Ile | Leu | Thr | Arg | Gln | Glu | Gly | Tyr | Pro | Cys | Val | Phe | Tyr | Gly | Asp |
| | | 355 | | | | | 360 | | | | | 365 | | | |
| Tyr | Tyr | Gly | Ile | Pro | Gln | Tyr | Asn | Ile | Pro | Ser | Leu | Lys | Ser | Lys | Ile |
| | 370 | | | | | 375 | | | | | 380 | | | | |

```
Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
            405                 410                 415

Thr Glu Lys Pro Gly Ser Gly Leu Ala Ala Leu Ile Thr Asp Gly Pro
        420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 18
<211> LENGTH: 485
<212> TYPE: PRT
<213> ORGANISM: Bacillus

<400> SEQUENCE: 18

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Asn Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240
```

-continued

```
Ile Lys Tyr Ser Tyr Thr Arg Asp Trp Leu Thr His Val Arg Asn Thr
                245                 250                 255
Thr Gly Lys Pro Met Phe Ala Val Ala Glu Phe Trp Lys Asn Asp Leu
            260                 265                 270
Ala Ala Ile Glu Asn Tyr Leu Asn Lys Thr Ser Trp Asn His Ser Val
        275                 280                 285
Phe Asp Val Pro Leu His Tyr Asn Leu Tyr Asn Ala Ser Asn Ser Gly
    290                 295                 300
Gly Tyr Phe Asp Met Arg Asn Ile Leu Asn Gly Ser Val Val Gln Lys
305                 310                 315                 320
His Pro Ile His Ala Val Thr Phe Val Asp Asn His Asp Ser Gln Pro
                325                 330                 335
Gly Glu Ala Leu Glu Ser Phe Val Gln Ser Trp Phe Lys Pro Leu Ala
            340                 345                 350
Tyr Ala Leu Ile Leu Thr Arg Glu Gln Gly Tyr Pro Ser Val Phe Tyr
        355                 360                 365
Gly Asp Tyr Tyr Gly Ile Pro Thr His Gly Val Pro Ser Met Lys Ser
    370                 375                 380
Lys Ile Asp Pro Leu Leu Gln Ala Arg Gln Thr Tyr Ala Tyr Gly Thr
385                 390                 395                 400
Gln His Asp Tyr Phe Asp His His Asp Ile Ile Gly Trp Thr Arg Glu
                405                 410                 415
Gly Asp Ser Ser His Pro Asn Ser Gly Leu Ala Thr Ile Met Ser Asp
            420                 425                 430
Gly Pro Gly Gly Asn Lys Trp Met Tyr Val Gly Lys His Lys Ala Gly
        435                 440                 445
Gln Val Trp Arg Asp Ile Thr Gly Asn Arg Ser Gly Thr Val Thr Ile
    450                 455                 460
Asn Ala Asp Gly Trp Gly Asn Phe Thr Val Asn Gly Gly Ala Val Ser
465                 470                 475                 480
Val Trp Val Lys Gln
            485
```

<210> SEQ ID NO 19
<211> LENGTH: 485
<212> TYPE: PRT
<213> ORGANISM: Bacillus

<400> SEQUENCE: 19

```
His His Asn Gly Thr Asn Gly Thr Met Met Gln Tyr Phe Glu Trp Tyr
1               5                   10                  15
Leu Pro Asn Asp Gly Asn His Trp Asn Arg Leu Arg Asp Asp Ala Ala
            20                  25                  30
Asn Leu Lys Ser Lys Gly Ile Thr Ala Val Trp Ile Pro Pro Ala Trp
        35                  40                  45
Lys Gly Thr Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Asn Gln Leu Gln Ala Ala Val Thr Ser Leu Lys Asn Asn Gly
                85                  90                  95
Ile Gln Val Tyr Gly Asp Val Val Met Asn His Lys Gly Gly Ala Asp
            100                 105                 110
Gly Thr Glu Ile Val Asn Ala Val Glu Val Asn Arg Ser Asn Arg Asn
        115                 120                 125
```

```
Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 20
<211> LENGTH: 405
<212> TYPE: PRT
<213> ORGANISM: Bacillus

<400> SEQUENCE: 20

His His Asn Gly Thr Asn Gly Thr Met Met Gln Tyr Phe Glu Trp His
1               5                   10                  15
```

-continued

```
Leu Pro Asn Asp Gly Asn His Trp Asn Arg Leu Arg Asp Asp Ala Ser
             20                  25                  30

Asn Leu Arg Asn Arg Gly Ile Thr Ala Ile Trp Ile Pro Pro Ala Trp
         35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
             85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
            130                 135                 140

Phe Pro Gly Arg Gly Asn Thr Tyr Ser Asp Phe Lys Trp Arg Trp Tyr
145                 150                 155                 160

Ile Lys Tyr Ser Phe Thr Arg Asp Trp Leu Thr His Val Arg Asn Ala
                165                 170                 175

Thr Gly Lys Glu Met Phe Ala Val Ala Glu Phe Trp Lys Asn Asp Leu
            180                 185                 190

Gly Ala Leu Glu Asn Tyr Leu Asn Lys Thr Asn Trp Asn His Ser Val
            195                 200                 205

Phe Asp Val Pro Leu His Tyr Asn Leu Tyr Asn Ala Ser Asn Ser Gly
210                 215                 220

Gly Asn Tyr Asp Met Ala Lys Leu Leu Asn Gly Thr Val Val Gln Lys
225                 230                 235                 240

His Pro Met His Ala Val Thr Phe Val Asp Asn His Asp Ser Gln Pro
            245                 250                 255

Gly Glu Ser Leu Glu Ser Phe Val Gln Glu Trp Phe Lys Pro Leu Ala
            260                 265                 270

Tyr Ala Leu Ile Leu Thr Arg Glu Gln Gly Tyr Pro Ser Val Phe Tyr
            275                 280                 285

Gly Asp Tyr Tyr Gly Ile Pro Thr His Ser Val Pro Ala Met Lys Ala
            290                 295                 300

Lys Ile Asp Pro Ile Leu Glu Ala Arg Gln Asn Phe Ala Tyr Gly Thr
305                 310                 315                 320

Gln His Asp Tyr Phe Asp His His Asn Ile Ile Gly Trp Thr Arg Glu
            325                 330                 335

Gly Asn Thr Thr His Pro Asn Ser Gly Leu Ala Thr Ile Met Ser Asp
            340                 345                 350

Gly Pro Gly Gly Glu Lys Trp Met Tyr Val Gly Gln Asn Lys Ala Gly
            355                 360                 365

Gln Val Trp His Asp Ile Thr Gly Asn Lys Pro Gly Thr Val Thr Ile
            370                 375                 380

Asn Ala Asp Gly Trp Ala Asn Phe Ser Val Asn Gly Gly Ser Val Ser
385                 390                 395                 400

Ile Trp Val Lys Arg
            405
```

```
<210> SEQ ID NO 21
<211> LENGTH: 483
<212> TYPE: PRT
<213> ORGANISM: Bacillus

<400> SEQUENCE: 21

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65              70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145             150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225             230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305             310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380
```

```
Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg
```

POLYPEPTIDES HAVING ALKALINE α-AMYLASE ACTIVITY

BACKGROUND OF THE INVENTION

1. Field of the Invention

The present invention relates to isolated polypeptides having α-amylase activity and isolated nucleic acid sequences encoding the polypeptides. Further, the invention relates to variants of the α-amylases of the invention. The invention also relates to nucleic acid constructs, vectors, and host cells comprising the nucleic acid sequences as well as methods for producing and using the polypeptides.

2. Description of the Related Art

For a number of years α-amylase enzymes have been used for a variety of different purposes, the most important of which are starch liquefaction, textile desizing, starch modification in the paper and pulp industry, and for brewing and baking. A further use of α-amylases, which is becoming increasingly important is the removal of starchy stains during washing with a detergent at alkaline pH.

Examples of commercial α-amylase products are Termamyl®, Duramyl™, BAN® and Fungamyl®, all available from Novo Nordisk A/S, Denmark. These and similar products from other commercial sources have an acidic to a neutral pH optimum, typically in the range of from pH 5 to pH 7.5, and they do not display optimal activity in detergent solutions at alkaline pH.

WO 95/26397 discloses an α-amylase from a Bacillus strain which has optimum activity at pH 8. WO 96/23873 describes variants of Bacillus amylases with improved performance under washing conditions.

U.S. Pat. No. 5,147,796 describes an alkaline pullulanase having alpha-amylase activity. FIG. 2b of the document shows optimum amylase activity at pH 8–8.5.

M. Takagi et al., J. Ferment. Bioeng., vol 81, No. 6, 557–559 (1996) describe an alkaliphilic alpha-amylase-pullulanase from Bacillus sp. The enzyme has optimum amylase activity at pH 9, but the activity drops rapidly at higher pH, and the activity at pH 10 is lower than at pH 7.

WO 97/00324 (KAO) disclose a gene encoding an alkaline liquefying α-amylase derived from Bacillus sp. strain KSM-AP1378 with the deposited no. FERM BP-3048 suitable for detergents.

It is an object of the present invention to provide novel α-amylases with improved performance in alkaline solutions, especially in alkaline detergent solutions at pH around 9–11.

SUMMARY OF THE INVENTION

The present invention relates to isolated polypeptides having α-amylase activity selected from the group consisting of:

(a) a polypeptide having an amino acid sequence which has at least 85% identity with amino acids for mature polypeptide amino acids 1 to 485 of SEQ ID NO:2 or SEQ ID NO: 4;

(b) a polypeptide encoded by a nucleic acid sequence which hybridizes under medium stringency conditions with (i) the nucleic acid sequence of SEQ ID NO:1 or SEQ ID NO: 3, (ii) the cDNA sequence of SEQ ID NO:1 or SEQ ID NO:3, (iii) a subsequence of (i) or (ii) of at least 100 nucleotides, or (iv) a complementary strand of (i), (ii), or (iii);

(c) an allelic variant of (a) or (b);

(d) a fragment of (a), (b) or (c) that has α-amylase activity;

(e) a polypeptide having improved wash performance in alkaline detergent solutions, especially in alkaline detergent solutions at a pH around 9–11, and more preferably, at a pH around 9–10.5;

(f) a temperature optimum determined using the Phadebas method (pH 9.0) in the range between 55 to 65° C.; and (g) a pI between 7–8 determined by isoelectric focusing (Pharmacia, Ampholine, pH 35–9.3).

Further the invention relates to variants of the α-amylase of the invention. The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

The present invention is further illustrated with reference to the accompanying drawings, in which:

FIG. 1 shows the alignment of a number of Bacillus α-amylases, namely, 707amy (SEQ ID NO:13); AA-I10 (SEQ ID NO:14); AA-I6 (SEQ ID NO:15); BAN (SEQ ID NO:16); BSG (SEQ ID NO:17); AP1378 (SEQ ID NO:18); SP690 (SEQ ID NO:19); SP722 (SEQ ID NO:20); Term (SEQ ID NO:21).

DETAILED DESCRIPTION OF THE INVENTION

Microbial Source

Figure 2:
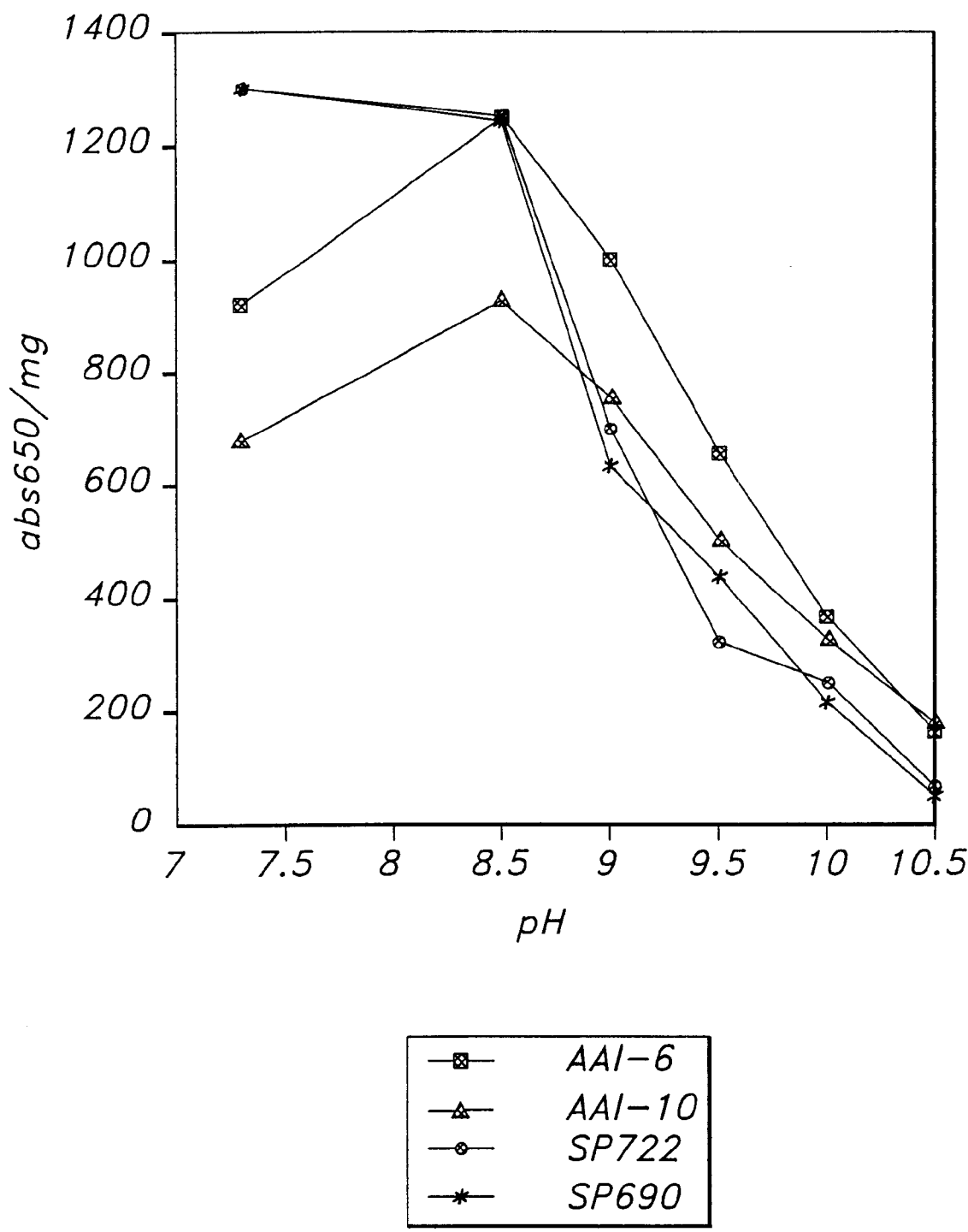
FIG. 2 shows the pH Profile of the α-amylases AAI-6 and AAI-10 compared to α-amylases SP722 and SP690. The activity is shown in absolute values as Abs650/mg. The pH profile is measured at 37° C.

The alkaline α-amylases of the invention may be derived from a strain of Bacillus. Preferred strains are of Bacillus sp. DSM 12650 (the AAI-6 α-amylase) or DSM 12651 (the AAI-10 α-amylase). These strains were deposited on Jan. 25, 1999 by the inventors under the terms of the Budapest Treaty on the International Recognition of the Deposit of Microorganisms for the Purposes of Patent Procedure at Deutshe Samnunmlung von Microorganismen und Zellkulturen GmbH (DSMZ), Mascheroder Weg 1b, D-38124 Braunschweig DE.

*Escherichia coli* strains termed NN049469 and NN049468 containing the α-amylase genes in plasmids pLiH1300 (AAI 6) and pLiH1298 (AAI10), respectively, have also been deposited on Apr. 7, 1999 under the terms of the Budapest Treaty with the Deutshe Sammmlung von Microorganismen und Zellkulturen GmbH (DSMZ), Mascheroder Weg 1b, D-38124 Braunschweig DE, and given the accession numbers DSM12763 and DSM12762, respectively.

Polypeptides Having α-amylase Activity

α-Amylases (α-1,4-glucan-4-glucanohydrolases, EC 3.2.1.1) constitute a group of enzymes which catalyze hydrolysis of starch and other linear and branched 1,4-glucosidic oligo- and polysaccharides. For purposes of the present invention, α-amylase activity is determined using the Phadebas assay or the pNPG7 assay described below in the "Materials and Methods" section.

Homology of Enzyme

In a first embodiment, the present invention relates to isolated polypeptides having an amino acid sequence which has a degree of identity to amino acids 1 to 485 of SEQ ID NO:2 or SEQ ID NO:4 (i.e., the mature polypeptides) of at least about 85%, preferably at least about 90%, preferably at least about 93%, more preferably at least about 95%, even more preferably at least 97%, and most preferably 99% which have α-amylase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 1 to 485 of SEQ ID NO:2 or SEQ ID NO:4.

The amino acid sequence homology may be determined as the degree of identity between the two sequences indicating a derivation of the first sequence from the second. The homology may suitably be determined by means of computer programs known in the art. Thus, GAP provided in GCG version 8 (Needleman, S. B. and Wunsch, C. D., (1970), Journal of Molecular Biology, 48, 443–453) may be used for a pairwise alignment of the sequences and calculation of the degree of identity or degree of homology using the default settings. Alternatively, Gap from GCG version 9 may be used with a translated version 8 peptide scoring matrix, a gap creation penalty of 30, a gap extension penalty of 1 using ntol's matrix (http://plasmid/~bioweb/matrix/) without end gap penalty.

Homology to Known Bacillus sp. α-amylases

A homology search of known sequences showed homologies for the sequences of the invention with a number of Bacillus amylases in the range 67–81% on amino acid determined as described above.

Specifically, homologous α-amylases to the sequences of the invention (i.e., SEQ ID NO: 2 and SEQ ID NO: 4) are SP690 (SEQ ID NO: 1 of U.S. Pat. No. 5,856,164 which is about 81% homologous), SP722 (SEQ ID NO: 2 of U.S. Pat. No. 5,856,164 which is about 81% homologous) and the mature part (amino acids 31–516) of the α-amylase obtained from Bacillus sp. KIM-AP1378 disclosed as SEQ ID NO: 2 of WO 97/00324 which is about 81% homologous to the sequences of the invention.

Preferably, the polypeptides of the present invention comprise the amino acid sequence of SEQ ID NO:2 or SEQ ID NO:4 or an allelic variant thereof, or a fragment thereof that has α-amylase activity. SEQ ID NO: 2 or SEQ ID NO: 4 show the mature part the alkaline α-amylases of the invention.

A fragment of SEQ ID NO:2 or SEQ ID NO: 4 are polypeptides having one or more amino acids deleted from the amino and/or carboxyl terminus of this amino acid sequence.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the homologous polypeptides may differ from the amino acid sequence of SEQ ID NO:2 or SEQ ID NO:4 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having α-amylase activity which are encoded by nucleic acid sequences which hybridize under medium stringency conditions, more preferably medium-high stringency conditions, even more preferably high stringency conditions, and most preferably very high stringency conditions with a nucleic acid probe which hybridizes under the same conditions with (i) the nucleic acid sequence of SEQ ID NO:1 or SEQ ID NO:3, (ii) the cDNA sequence of SEQ ID NO:1 or SEQ ID NO:3, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO:1 or SEQ ID NO:3 may be at least 100 nucleotides or preferably at least 200 nucleotides. Moreover, the subsequence may encode a polypeptide fragment which has α-amylase activity. The polypeptides may also be allelic variants or fragments of the polypeptides that have α-amylase activity.

The nucleic acid sequence of SEQ ID NO:1 or SEQ ID NO:3 or a subsequence thereof, as well as the amino acid sequence of SEQ ID NO:2 or SEQ ID NO: 4 or a fragment thereof, may be used to design a nucleic acid probe to identify and clone DNA encoding polypeptides having α-amylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having α-amylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or SEQ ID NO:3 or subsequences thereof, the carrier material is used in a Southern blot. For purposes of the present invention, hybridization indicates that the nucleic acid sequence hybridizes to a nucleic acid probe corresponding to the nucleic acid sequence shown in SEQ ID NO:1 or SEQ ID NO: 3, its complementary strand, or a subsequence thereof, under medium to very high stringency conditions. Molecules to which the nucleic acid probe hybridizes under these conditions are detected using X-ray film.

In another preferred embodiment, the nucleic acid probe is the nucleic acid sequence contained in plasmids pLiH1300 (AAI6) or pLiH1298 (AAI10), respectively, which are contained in *Escherichia coli* DSM12763 or *Escherichia coli* DSM12762, respectively, or, wherein the nucleic acid sequence encodes a polypeptide having acid α-amylase activity of the invention and shown in SEQ ID NO: 2 or SEQ ID NO: 4, respectively.

For long probes of at least 100 nucleotides in length, medium to very high stringency conditions are defined as prehybridization and hybridization at 42° C. in 5×SSPE, 0.3% SDS, 200 µg/ml sheared and denatured salmon sperm DNA, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 55° C. (medium stringency), preferably at least at 60° C. (medium-high stringency), more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to isolated polypeptides, i.e., the polypeptides shown in SEQ ID NO: 2 or SEQ ID NO: 4, having the following physico-chemical properties:

A temperature optimum (see FIG. 3) determined using the Phadebas method (pH 9.0) in the range between 55 and 65° C., more precisely at about 60° C.

A pI for AAI-6 determined using isoelectric focusing was found to be between 7–7.3, and the pI for AAI-10 was found to be between 7–8.

The polypeptides of the present invention have at least 20%, preferably at least 40%, more preferably at least 60%, even more preferably at least 80%, even more preferably at least 90%, and most preferably at least 100% of the α-amylase activity of the mature polypeptide of SEQ ID NO: 2 or SEQ ID NO: 4.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulars, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

In another preferred embodiment, the polypeptide is a Bacillus sp. polypeptide, more preferred embodiment, the polypeptide is a Bacillus sp. DSM 12650 and Bacillus sp. DSM 12651 polypeptide, e.g., the polypeptide with the amino acid sequence of SEQ ID NO: 2 or SEQ ID NO: 4, respectively.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-α-amylase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Mutant α-amylases

Invention also relates to a mutant of the α-amylases shown in SEQ ID NO: 2 or SEQ ID NO: 4. The mutant α-amylase of to the invention is characterized by the fact that one or more of the methionine amino acid residues is exhanged with any amino acid residue except for Cys and Met. Thus, according to the invention the amino acid residues to replace the methionine amino acid residue are the following: Ala, Arg, Asn, Asp, Gln, Glu, Gly, His, Ile, Leu, Lys, Phe, Pro, Ser, Thr, Trp, Tyr, and Val.

A preferred embodiment of the mutant α-amylase of the invention is characterized by the fact that one or more of the methionine amino acid residues is (are) exchanged with a Leu, Thr, Ala, Gly, Ser, Ile, or Asp amino acid residue, preferably a Leu, Thr, Ala, or Gly amino acid residue. In this embodiment a very satisfactory activity level and stability in the presence of oxidizing agents is obtained. Specifically this means that one or more of the methionines in the following position may be replaced or deleted using any suitable technique known in the art, including especially site directed mutagenesis and gene shuffling. Contemplated positions in SEQ ID NO: 2 are: 10, 105, 202, 208, 246, 286, 309, 430, 440 and positions in SEQ ID NO: 4 are: 10, 105, 202, 208, 246, 286, 309, 430, 440, 454.

In a preferred embodiment of the mutant α-amylase of the invention is characterized by the fact that the methionine amino acid residue at position 202 is exchanged with any of amino acid residue expect for Cys and Met, preferably with a Leu, Thr, Ala, Gly, Ser, Ile, or Asp.

Other contemplated preferred mutations include deletion of one, two or more residues of amino acids R181, G182, D183 or G184, K185, G186 or substitution of one or more of these residues. A preferred mutation is the deletion of D183–G184. Particularly relevant mutations are substitutions of G186 with Ala, Arg, Asn, Asp, Cys, Gln, Glu, His, Ile, Leu, Lys, Met, Phe, Pro, Ser, Thr, Trp, Tyr, and Val. A particularly preferred substitution is G186R.

Also contemplated is substitution of N195 with Ala, Arg, Asn, Asp, Cys, Gln, Glu, Gly, His, Ile, Leu, Lys, Met, Phe, Pro, Ser, Thr, Trp, Tyr, and Val. A particularly interesting substitution is N195F.

The following combinations of the above metioned mutations include: deletion of D183–G184+N195F, deletion of D183–G184+G186R, deletion of D183–G184+G186R+N195F and G186R+N195F.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pLIH1300 (AAA16) or plasmid LiH1298 (AAI10), respectively, that is contained in *Escherichia coli* DSM12763 and *Escherichia coli* DSM12762, respectively. In another preferred embodiment, the nucleic acid sequence is the mature polypeptide coding region of SEQ ID NO: 1 or SEQ ID NO: 3. The present invention also encompasses nucleic acid sequences which encode a polypeptide having the amino acid sequence of SEQ ID NO:2 or SEQ ID NO: 4 which differ from SEQ ID NO: 1 or SEQ ID NO: 3 by virtue of the degeneracy of the genetic code. The present invention also relates to subsequences of SEQ ID NO:1 or SEQ ID NO: 3 which encode fragments of SEQ ID NO: 2 or SEQ ID NO: 4, respectively, that have α-amylase activity.

Subsequences of SEQ ID NO: 1 or SEQ ID NO: 3 are nucleic acid sequences encompassed by SEQ ID NO:1 or SEQ ID NO: 3 except that one or more nucleotides from the 5' and/or 3' end have been deleted.

The present invention also relates to mutant nucleic acid sequences comprising at least one mutation in the mature polypeptide coding sequence of SEQ ID NO: 1 or SEQ ID NO: 3, in which the mutant nucleic acid sequence encodes a polypeptide which consists of amino acids 1 to 485 of SEQ ID NO: 2 or SEQ ID NO: 4.

The techniques used to isolate or clone a nucleic acid sequence encoding a polypeptide are known in the art and include isolation from genomic DNA, preparation from cDNA, or a combination thereof The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Bacillus, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Homology of DNA Sequences Encoding the Enzyme

The present invention also relates to nucleic acid sequences which have a degree of homology to the mature polypeptide coding sequence of SEQ ID NO:1 (i.e., nucleotides 1 to 1458) or SEQ ID NO: 3 (i.e., nucleotide 1 to 1458) of at least about 85% homology on DNA level, preferably about 90%, more preferably about 93%, more preferably about 95%, even more preferably about 97%, and most preferably about 99% homology, which encodes an active polypeptide.

The DNA sequence homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the following default parameters: GAP creation penalty of 5.0 and GAP extension penalty of 0.3, default scoring matrix. GAP uses the method of Needleman/Wunsch/Sellers to make alignments.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1 or SEQ ID NO: 3, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for α-amylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under medium stringency conditions, preferably medium-high stringency conditions, more preferably high stringency conditions, and most preferably very high stringency conditions with a nucleic acid probe which hybridizes under the same conditions with the nucleic acid sequence of SEQ ID NO:1 or SEQ ID NO: 3 or its complementary strand; or allelic variants and subsequences thereof (Sambrook et al., 1989, supra), as defined herein.

The present invention also relates to isolated nucleic acid sequences produced by (a) hybridizing a DNA under medium, medium-high, high, or very high stringency conditions with the sequence of SEQ ID NO:1 or SEQ ID NO: 3, or their complementary strands, or a subsequence thereof, and (b) isolating the nucleic acid sequence. The subsequence is preferably a sequence of at least 100 nucleotides such as a sequence which encodes a polypeptide fragment which has α-amylase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO: 1 or SEQ ID NO: 3 or a subsequence thereof, wherein the mutant nucleic acid sequence encodes a polypeptide which consists of 1 to 485 of SEQ ID NO: 2 or SEQ ID NO: 4 or a fragment thereof which has α-amylase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. These other procedures include gene shuffling, e.g., as described in WO 95/22625 (from Affymax Technologies N.V.) and WO 96/00343 (from Novo Nordisk A/S).

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

Promoter Sequence

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al, 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Terminator Sequence

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Signal Peptide

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Regulatory System

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fimgi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis,* or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus.*

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

Methods of Production

The present invention also relates to methods for producing a polypeptide of the present invention comprising (a)

cultivating a strain, which in its wild-type form is capable of producing the polypeptide, to produce a supernatant comprising the polypeptide; and (b) recovering the polypeptide. Preferably, the strain is of the genus Bacillus sp.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO:1 or SEQ ID NO: 3, wherein the mutant nucleic acid sequence encodes a polypeptide which consists of amino acids 1 to 485 of SEQ ID NO:2 or SEQ ID NO: 4, and (b) recovering the polypeptide.

Compositions

In a still further aspect, the present invention relates to compositions comprising a polypeptide of the present invention. Preferably, the compositions are enriched in a polypeptide of the present invention. In the present context, the term "enriched" indicates that the α-amylase activity of the composition has been increased, e.g., with an enrichment factor of 1.1.

The composition may comprise a polypeptide of the invention as the major enzymatic component, e.g., a monocomponent composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably *Aspergillus aculeatus, Aspergillus awamori, Aspergillus niger,* or *Aspergillus oryzae,* or Trichoderma, Humicola, preferably *Humicola insolens,* or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Industrial Applications

Owing to their activity at alkaline pH values, the α-amylases of the invention are well suited for use in a variety of industrial processes, in particular the enzyme finds potential applications as a component in detergents, e.g., laundry and hard surface cleaning detergent compositions, but it may also be useful in the production of sweeteners and ethanol from starch. Thus, it may be used in conventional starch-converting processes, such as liquefaction and saccharification processes described in U.S. Pat. No. 3,912,590 and EP patent publications Nos. 252,730 and 63,909.

The alkaline α-amylases of the invention may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The α-amylases of the invention is especially useful in a process for producing a papermaking pulp from starch-coated printed paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The α-amylases of the invention may also be very useful in modifying starch where enzymatically modified starch is used in papermaking together with alkaline fillers such as calcium carbonate, kaolin and clays. With the alkaline a-amylases of the invention it becomes possible to modify the starch in the presence of the filler thus allowing for a simpler integrated process.

The α-amylases of the invention may also be very useful in textile desizing. In the textile processing industry, a-amylases are traditionally used as auxiliaries in the desizing process to facilitate the removal of starch-containing size which has served as a protective coating on weft yarns during weaving. Complete removal of the size coating after weaving is import-ant to ensure optimum results in the subsequent processes, in which the fabric is scoured, bleached and dyed. Enzymatic starch break-down is preferred because it does not involve any harmful effect on the fiber material. In order to reduce processing cost and increase mill through-put, the desizing processing is sometimes combined with the scouring and bleaching steps. In such cases, non-enzymatic auxiliaries such as alkali or oxidation agents are typically used to break down the starch, because traditional a-amylases are not very compatible with high pH levels and bleaching agents. The non-enzymatic breakdown of the starch size does lead to some fiber damage because of the rather aggressive chemicals used. Accordingly, it would be desirable to use the a-amylases of the invention as they have an improved performance in alkaline solutions. The a-amylases may be used alone or in combination with a cellulase when desizing cellulose-containing fabric or textile.

The α-amylases of the invention may also be very useful in a beer-making process; the α-amylases will typically be added during the mashing process.

Detergent Compositions

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect oxp™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g., from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g. a special strain of *B. licheniformis,* described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from Humicola insolens, Myceliophthora thermophila and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus,* and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liqour, preferably 0.05–5 mg of enzyme protein per liter of wash liqour, in particular 0.1–1 mg of enzyme protein per liter of wash liqour.

The enzyme of the invention may additionally be incorporated in the detergent formulations disclosed in WO 97/07202 which is hereby incorporated as reference.

Dishwash Detergent Compositions

The enzyme of the invention mat also be used in dish wash detergent compositions, including the following:

| 1) POWDER AUTOMATIC DISHWASHING COMPOSITION | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetyl ethylene diamine (TAED) | 1–4% |
| Sodium sulphate | 5–33% |
| Enzymes | 0.0001–0.1% |

| 2) POWDER AUTOMATIC DISHWASHING COMPOSITION | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetyl ethylene diamine (TAED) | 1–2% |
| Polyacrylate polymer (e.g. maleic acid/acrylic acid copolymer) | 6–25% |
| Enzymes | 0.0001–0.1% |
| Perfume | 0.1–0.5% |
| Water | 5–10 |

| 3) POWDER AUTOMATIC DISHWASHING COMPOSITION | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetyl ethylene diamine (TAED) | 0–6% |
| Maleic acid/acrylic acid copolymer | 0–5% |
| Clay | 1–3% |
| Polyamino acids | 0–20% |
| Sodium polyacrylate | 0–8% |
| Enzymes | 0.0001–0.1% |

| 4) POWDER AUTOMATIC DISHWASHING COMPOSITION | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetyl ethylene diamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

| 5) POWDER AUTOMATIC DISHWASHING COMPOSITION | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylene triamine pentaacetate, pentasodium salt | 0–2.5% |
| Enzymes | 0.0001–0.1% |
| Sodium sulphate, water | Balance |

| 6) POWDER AND LIQUID DISHWASHING COMPOSITION WITH CLEANING SURFACTANT SYSTEM | |
|---|---|
| Nonionic surfactant | 0–1.5% |
| Octadecyl dimethylamine N-oxide dihydrate | 0–5% |
| 80:20 wt. C18/C16 blend of octadecyl dimethylamine N-oxide dihydrate and hexadecyldimethyl amine N-oxide dihydrate | 0–4% |

| | |
|---|---|
| 70:30 wt. C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetyl ethylene diamine (TAED) | 0–4% |
| Maleic acid/acrylic acid copolymer | 0–7.5% |
| Sodium sulphate | 0–12.5% |
| Enzymes | 0.0001–0.1% |
| 7) NON-AQUEOUS LIQUID AUTOMATIC DISHWASHING COMPOSITION | |
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |
| 8) NON-AQUEOUS LIQUID DISHWASHING COMPOSITION | |
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |
| 9) THIXOTROPIC LIQUID AUTOMATIC DISHWASHING COMPOSITION | |
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |
| 10) LIQUID AUTOMATIC DISHWASHING COMPOSITION | |
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetyl ethylene diamine (TAED) | 0–8% |
| Maleic acid/acrylic acid copolymer | 4–8% |
| Enzymes | 0.0001–0.1% |
| 11) LIQUID AUTOMATIC DISHWASHING COMPOSITION CONTAINING PROTECTED BLEACH PARTICLES | |
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

11) Automatic dishwashing compositions as described in 1), 2), 3), 4), 6) and 10), wherein perborate is replaced by percarbonate.

12) Automatic dishwashing compositions as described in 1)–6) which additionally contain a manganese catalyst. The manganese catalyst may, e.g., be one of the compounds described in "Efficient manganese catalysts for low-temperature bleaching", Nature 369, 1994, pp. 637–639.

Uses

The present invention is also directed to methods for using the polypeptides having α-amylase activity in detergent compositions, in particular laundry detergent compositions and dishwash detergent compositions.

The present invention is further described by the following examples which should not be construed as limiting the scope of the invention.

Materials and Methods

Chemicals used as buffers and substrates were commercial products of at least reagent grade.

Materials

Enzymes

SP690: α-amylase disclosed in SEQ ID NO: 1 of U.S. Pat. No. 5,856,164.

SP722: α-amylase disclosed in SEQ ID NO: 2 of U.S. Pat. No. 5,856,164.

Termamyl®: α-amylase from Bacillus licheniformis disclosed in SEQ ID NO: 1 of U.S. Pat. No. 5,830,837.

AAI-10: α-amylase of the invention shown in SEQ ID NO: 2.

AAI-6: α-amylase of the invention shown in SEQ ID NO: 4.

Model detergent

A/P (Asia/Pacific) Model Detergent has the following composition: 20% STPP (sodium tripolyphosphate), 25% $Na_2SO_4$, 15% $Na_2CO_3$, 20% LAS (linear alkylbenzene sulfonate, Nansa 80S), 5% $C_{12}$–$C_{15}$ alcohol ethoxylate (Dobanol 25-7), 5% $Na_2Si_2O_5$, 0.3% NaCl.

Omo Multi Acao (Brazil),

Omo concentrated powder (EU) (Unilever)

Ariel Futur liquid (EU) (Procter and Gamble)

Deposit of Biological Material

The following biological material has been deposited under the terms of the Budapest Treaty with the Deutshe Sammmlung von Microorganismen und Zellkulturen GmbH (DSMZ), Mascheroder Weg 1b, D-38124 Braunschweig DE, and given the following accession number:

| Deposit | Accession Number | Date of Deposit |
|---------|------------------|-----------------|
| NN17562 | DSM 12650 | January 25th 1999 |
| NN17563 | DSM 12651 | January 25th 1999 |
| NN049469 | DSM12763 | April 7th 1999 |
| NN049468 | DSM12762 | April 7th 1999 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Host Organism
Strain SHa273 disclosed in WO 95/10603
E. coli strain SJ2 (Diderichsen et al. (1990)).
Plasmids The gene bank vector was pSJ1678 which is further disclosed in WO 94/19454 which is hereby incorporated by reference.

Methods
General Molecular Biology Methods

Unless otherwise mentioned the DNA manipulations and transformations were performed using standard methods of molecular biology (Sambrook et al. (1989); Ausubel et al. (1995); Harwood and Cutting (1990).

Assays for α-Amylase Activity
1. Phadebas Assay

α-amylase activity is determined by a method employing Phadebas® tablets as substrate. Phadebas tablets (Phadebas® Amylase Test, supplied by Pharmacia Diagnostic) contain a cross-linked insoluble blue-colored starch polymer which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolyzed by the α-amylase giving soluble blue fragments. The absorbance of the resulting blue solution, measured spectrophotometrically at 620 nm, is a function of the α-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given α-amylase will hydrolyze a certain amount of substrate and a blue colour will be produced. The colour intensity is measured at 620 nm. The measured absorbance is directly proportional to the specific activity (activity/mg of pure α-amylase protein) of the α-amylase in question under the given set of conditions.

2. Alternative Method

α-amylase activity is determined by a method employing the PNP-G7 substrate. PNP-G7 which is a abbreviation for p-nitrophenyl-α,D-maltoheptaoside is a blocked oligosaccharide which can be cleaved by an endo-amylase. Following the cleavage, the α-Glucosidase included in the kit digest the substrate to liberate a free PNP molecule which has a yellow colour and thus can be measured by visible spectophometry at λ=405 nm. (400–420 nm.). Kits containing PNP-G7 substrate and α-Glucosidase is manufactured by Boehringer-Mannheim (cat.No. 1054635).

To prepare the substrate one bottle of substrate (BM 1442309) is added to 5 ml buffer (BM1442309). To prepare the α-Glucosidase one bottle of α-Glucosidase (BM 1462309) is added to 45 ml buffer (BM1442309). The working solution is made by mixing 5 ml α-Glucosidase solution with 0.5 ml substrate.

The assay is performed by transforming 20 μl enzyme solution to a 96 well microtitre plate and incubating at 25° C. 200 μl working solution, 25° C. is added. The solution is mixed and pre-incubated 1 minute and absorption is measured every 15 sec. over 3 minutes at OD 405 nm.

From the slope of the time dependent absorption-curve, the specific activity (activity per mg enzyme) of the α-amylase under the given conditions can be calculated using the Termamyl standard curve.

EXAMPLES

Example 1

Isolation of Genomic DNA of Strain DSM 12560 and DSM 12651

The strains Bacillus sp. DSM 12650 (the AAI-6 α-amylase) and Bacillus sp. DSM 12651(the AAI-10 α-amylase) were propagated in liquid TY medium (as described in Ausubel et al.(1995)). After 16 hours incubation at 37° C. and 300 rpm, the cells were harvested, and genomic DNA isolated by the method described by Pitcher et al. (1989).

Genomic Library Construction

Genomic DNA of strains above were partially digested with restriction enzyme Sau3A, and size-fractionated by electrophoresis on a 0.7% agarose gel. Fragments between 2 and 10 kb in size was isolated by electrophoresis onto DEAE-cellulose paper (Dretzen et al. (1981).

Isolated DNA fragments were ligated to BamHI digested pSJ1678 plasmid DNA, and the ligation mixture was used to transform E. coli SJ2.

Transformation

E. coli SJ2 host cells were prepared for and transformed by electroporation using a gene PULSER™ electroporator from BIO-RAD as described by the supplier.

Identification of Positive Transformants

DNA libraries in E. coli SJ2, constructed as described above, were screened on LB agar plates (described in Ausbel et al.(1995)) containing 0.5% AZCL-amylose (Megazyme) and 10 μg/ml Chloramphenicol and incubated overnight at 37° C. Clones expressing amylase activity appeared with blue diffusion haloes. One such clone expressing AAI-6 amylase was named LiH1300. Another clone expressing AAI-10 amylase was named LiH1298. The DNAs were further characterized by DNA sequencing of part of the cloned Sau3A DNA fragments.

Example 2

Determination of the DNA Sequence of the Gene Encoding Alpha Amylase from Strain DSM 12650 (AAI-6)

The clone constituting a large chromosomal fragment containing the gene encoding the amylolytic activity inserted into plasmid pSJ1678, pLiH1300, was used as template in an attempt to specifically PCR amplify internal DNA fragments of the amylase encoding gene by the use of degenerate primers directed towards the conserved regions in known Bacillus α-amylases.

The degenerate primers were directed towards the following regions/amino acid sequences:
For36: GITA(L/V/I)W(I/L) (SEQ ID NO. 5)
For97: VY(G/A)D(V/F/L)V(M/L/I/F)NH (SEQ ID NO. 6)
For227: DG(F/I)R(F/L/I/V)DA(A/V)KH (SEQ ID NO. 7)
Rev235: DG(F/I)R(F/L/I/V)DA(A/V)KH (SEQ ID NO. 8)
Rev328: VTFV(D/E)NHD (SEQ ID NO. 9)
Rev410: GWTREG (SEQ ID NO. 10)

The various combinations of forward (For) and reverse (Rev) primers were used in PCR and internal DNA fragments could be amplified.
The DNA fragments were purified by QIAquick spin colums (QUIGEN) and sequenced utilizing the same degenerate primers.
From this initial sequence the DNA sequence of the complete coding region of AAI-6 α-amylase SEQ ID NO:2 was determined by a standard primers-walking approach.

Example 3

Determination of the DNA Sequence of the Gene Encoding Alpha-amylase from Strain DSM 12651 (AAI-10)

The clone constituting a large chromosomal fragment containing the gene encoding the amylolytic activity inserted into plasmid pSJ1678, pLiH1298, was used as template in an attempt to specifically PCR amplify internal DNA fragments of the amylase encoding gene by the use of degenerate primers directed towards the conserved regions in known Bacillus alpha-amylases.

The degenerate primers were directed towards the following regions/amino acid sequences:
For36: GITA(L/V/I)W(I/L) (SEQ ID NO. 5)
For97: VY(G/A)D(V/F/L)V(M/L/I/F)NH (SEQ ID NO. 6)
For227: DG(F/I)R(F/L/I/V)DA(A/V)KH (SEQ ID NO. 7)
Rev235: DG(F/I)R(F/L/I/V)DA(A/V)KH (SEQ ID NO. 8)
Rev328: VTFV(D/E)NHD (SEQ ID NO. 9)
Rev410: GWTREG (SEQ ID NO. 10)

The various combinations of forward (For) and reverse (Rev) primers were used in PCR and internal DNA fragments could be amplified.
The DNA fragments were purified by QIAquick spin columns (QUIGEN) and sequenced utilizing the same degenerate primers.
From this initial sequence the DNA sequence (SEQ ID NO: 1 ) of the complete coding region of AAI-10 α-amylase (SEQ ID NO: 4) was determined by a standard primers-walking approach.

Example 4

Subcloning of DSM 12650(AAI-6) α-amylase into pTVB110 pTVB 110 is a plasmid replicating in Bacillus subtilis by the use of origin of replication from pUB110 (Gryczan, T. J. (1978) J. Bact. 134:318–329). The plasmid further encodes the cat gene, conferring resistance towards chloramphenicol, obtained from plasmid pC194 (Horinouchi, S. and Weisblum, B. (1982), J. Bact. 150: 815–825). The plasmid harbors a truncated version of the Bacillus licheniformis alpha amylase gene, amyL, such that the amyL promoter, signal sequence and transcription terminator are present but the plasmid does not provide an amy-plus phenotype (halo formation on starch containing agar).

In order to express high amount of the AAI-6 amylase the mature gene was fused precisely to the amyL signal sequence such that transcriptions is initiated by the amyL promoter and translocation is directed by the amyL signal sequence.

Primers 197cloningN and 197cloningC were used to amplify an approximately 1480 bp fragment by PCR on plasmid pLiH1300 using the Pwo polymerase under conditions recommended by the manufacturer (Boehringer Mannheim).

The resulting approximately 1480 bp fragment was digested with restriction endonucleases PstI and SfiI and ligated with plasmid digested with the same enzymes.

Protease and amylase deleted Bacillus subtilis strain SHa273 (disclosed in WO95/10603) was transformed with the ligation mixture and the DNA sequence of an amy-plus plus transformant was verified. This plasmid is denoted pTVB230.

Oligonucleotides
197cloningC
5' CCG AGC TCG GCC GGC TGG GCC GTC GAC TTA TCG TTT CAC CCA TAC GG (SEQ ID NO: 11)
197cloningN
5' CAT TCT GCA GCA GCG GCG CAT CAC GAT GGG ACG AAC GG (SEQ ID NO: 12)

Example 5

Subcloning of AAI-10 Alpha Amylase into pTVB110

DNA sequencing revealed a rather high identity between alpha-amylases from stains AAI-6 and AAI-10. Consequently the same oligonucleotides and strategy was utilized for the cloning of AAI- 10 alpha-amylase into expression vector pTVB110 resulting in plasmid pTVB229, which was then fermented using standard techniques.

Example 6

Purification of the AAI-6α-amylase

The culture broth was flocculated by adding 0.01 ml 50%(w/w) $CaCl_2$, $2H_2O$, 0.0 ml 12% (w/w) Sodium aluminate, 0.025 ml 10% C521 and 0.075 ml 0.1% A130 pr. ml culture broth. A clear solution was obtained after centrifugation. The enzyme solution was added ammonium sulphate to a final concentration of 1.2 M and applied on a Butyl Toyo Pearl column (100 ml) previously equilibrated in 1.2 M ammonium sulphate, 10 mM Tris-HCl, pH 7.0. The amylase was eluted using 5 mM Tris-HCl, pH 7.0 and the eluted pool was dialysed against 5 mM Tris-HCl over night. The fraction was then subjected to ion exchange chromatography using a Q-Sepharose column (200 ml) previously equilibrated in 20 mM Tris-HCl, pH 9.0. Unbound material was washed out with the equilibration buffer, and the amylase was eluted using a linear gradient 0–1 M NaCl, 20 mM Tris-HCl, pH 9.0. Purity of the amylase preparation was above 95% judged by SDS-PAGE.

Example 7

Purification of AAI-10 α-amylase

The culture broth was flocculated as described above. The enzyme solution was added ammonium sulphate to a final concentration of 1.2 M and applied on a Butyl Toyo Pearl column (100 ml) previously equilibrated in 1.2 M ammonium sulphate, 10 mM Tris-HCl, pH 7.0. 20% of the activity was eluted with 5 mM Tris-HCl, pH 7.0 and the rest with isopropanol. The combined pool was fractionated on a Q-Sepharose column (100 ml), pH 9.7. Unbound material was washed out with the equilibration buffer, and the amylase was eluted using a linear gradient 0–1 M NaCl, 20 mM Tris-HCl, pH 9.4. The amylase containing pool was finally fractionated on a S Sepharose column, pH 5.5. Purity of the amylase preparation was above 95% judged by SDS-PAGE.

Example 8

Characterization of the AAI-6 and AAI-10 α-amylase

The α-amylase activity was measured using both the Phadebas assay (37° C., pH 7.3) and the Alternative pNPG7 Assay (25° C., pH 7.1) described above. pH- and temperature profiles were made at selected pH- and temperature values. The pH-profile was measured at 37° C. and the temperature profile was measured at pH 9.0.

Isoelectric Point was determined using isoelectric focusing (Pharmacia, Ampholine, pH 3.5–9.3).

TABLE 1

Specific activity and pI

| Enzyme | mg/ml | NU/ml Phadebas 37° C. pH 7.3 | NU(T)/ml pNPG7, 25° C., pH 7.1 | pI |
|---|---|---|---|---|
| AAI-10 (SEQ NO: 4) | 0.4 | 17,500 | 12,000 | 7–8 |
| AAI-6 (SEQ ID NO: 2) | 0.6 | 25,000 | 13,500 | 7–7.3 |
| SP690 (SEQ ID NO: 1 of U.S. Pat. No. 5,856,164) | 8.2 | 35,000 | 6,000 | 7–9 |
| SP722 (SEQ ID NO: 2 of U.S. Pat. No. 5,856,164) | 2. | 35,000 | 7,000 | 5–6 |
| Termamyl ® | 12.4 | 7,000 | 7,000 | |

$E = 3.2 \text{ cm}^{-1} *(g/l)^{-1}$ for AA560, AAI-6 and AAI-10

Figure 3:
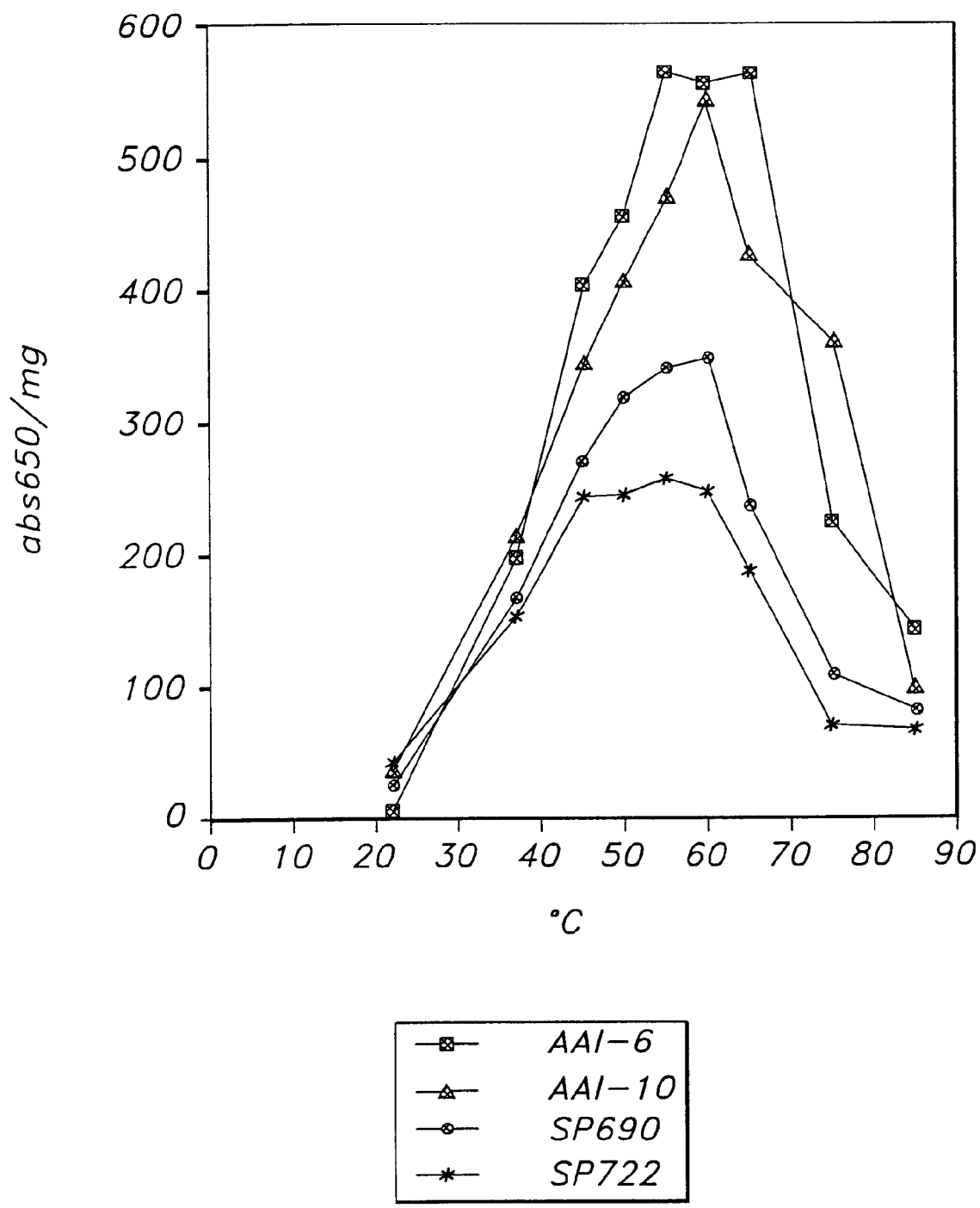
FIG. 3 shows the Temperature Profile of the α-amylases AAI-6 and AAI-10 at pH 9.0 compared to the reference α-amylases SP722 and SP690.
Figure 4:
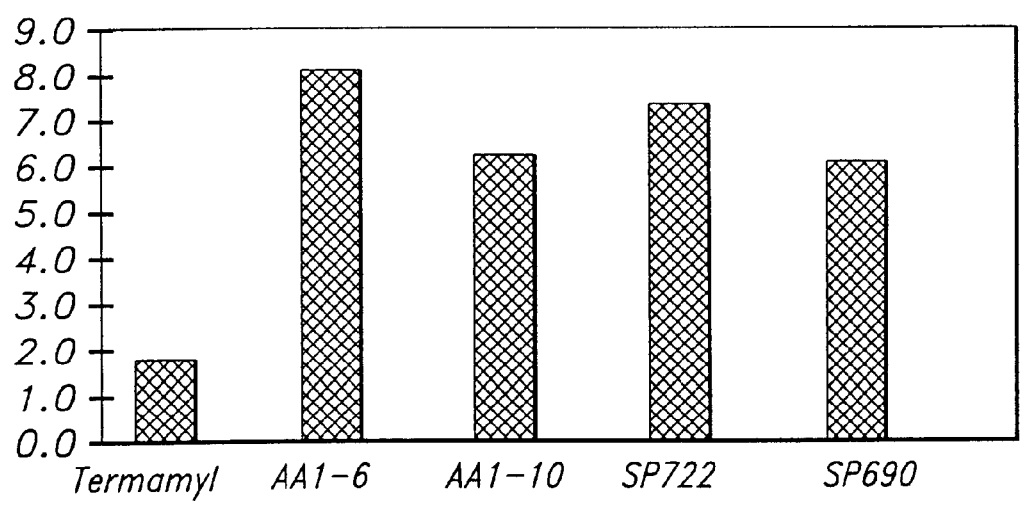
FIG. 4 shows the wash performance of AAI-6 and AAI-10 in the AP Model Detergent 97 in comparison to SP722, SP690 and Termamyl®.
Figure 5:
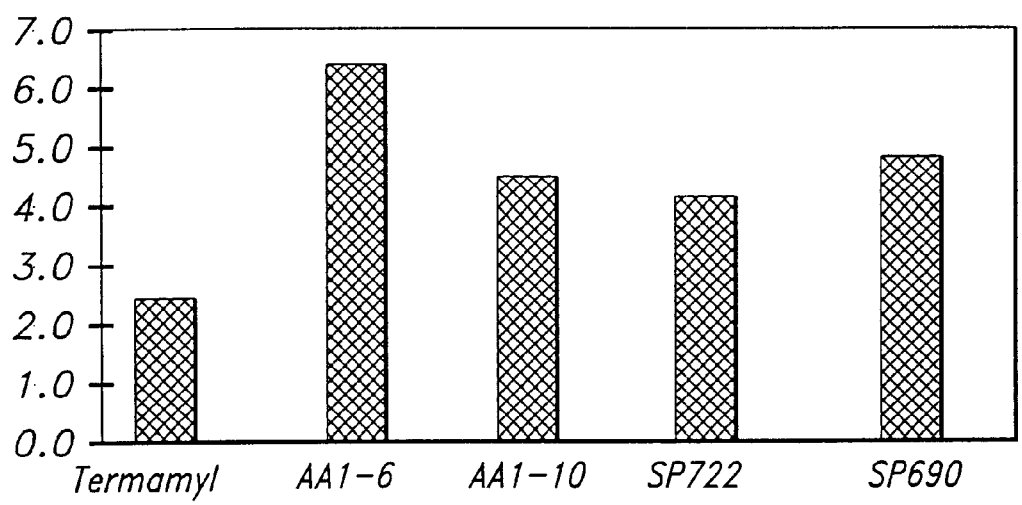
FIG. 5 shows the wash performance of AAI-6 and AAI-10 in Omo Multi Acao in comparison to SP722, SP690 and Termamyl®.
Figure 6:
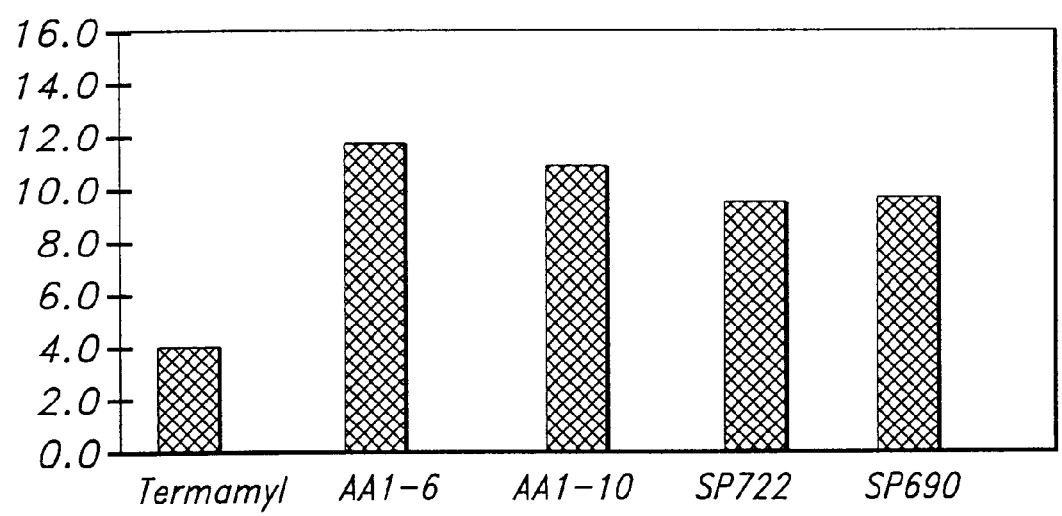
FIG. 6 shows the wash performance of AAI-6 and AAI-10 in Omo Concentrated in comparison to SP722, SP690 and Termamyl®.
Figure 7:
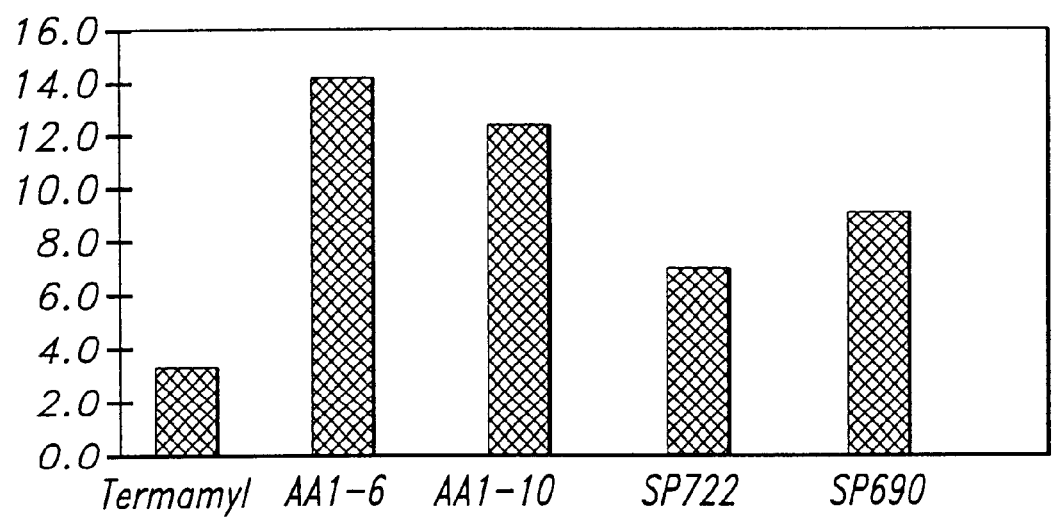
FIG. 7 shows the wash performance of AAI-6 and AAI-10 in Ariel Futur liquid in comparison to SP722, SP690 and Termamyl®.

The result of the pH-optimum determination and temperature optimum determination is shown in FIG. 2 and FIG. 3, respectively.

Example 9

Washing Test

Washing performance was evaluated by washing soiled test swatches at 15 and 30 minutes at 25 and 40° C. respectively in detergent solutions with the AAI-6 and AAI-10 α-amylase of the invention.

The detergents used are disclosed in Table 3 below. The A/P Model Detergent is described in the Materials section above. The other detergents are commercially available detergents. Commercial detergents containing amylase were inactivated by microwaves before wash.

The purified recombinant AAI-6 and AAI-10 α-amylases of Example 6 and 7 were added to the detergent solutions at the concentration indicated below. The test swatches were soiled with orange rice starch (CS-28 swatches available from CFT, Center for Test Material, Holland).

After washing, the swatches were evaluated by measuring the remission at 460 nm using a Elrepho Remission Spectrophotometer. The results are expressed as ΔR=remission of the swatch washed with the alpha-amylase minus the remission of a swatch washed at the same conditions without the alpha-amylase.

The results are shown in FIGS. 4–7. The results demonstrate that the α-amylase of the invention is effective in both detergents at highly alkaline pH.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

REFERENCES

Ausubel, F. M. et al. (eds.); Current protocols in Molecular Biology; 1995; John Wiley and Sons.

Sambrook et al.; Molecular Cloning: A Laboratory Manual; 1989,; Cold Spring Harbor Lab.; Cold Spring Harbor; N.Y.

Harwood C. R., and Cutting S. M. (eds.); Molecular Biological Methods for Bacillus; 1990; John Wiley and Sons.

Diderichsen B., Wedsted U., Hedegaard L., Jensen B. R., Sjøholm C.; Cloning of aldB, which encodes alpha-acetolactate decarboxylase, an exoenzyme from Bacillus brevis; J. Bacteriol., 1990, vol. 172, pp. 4315–4321.

Pitcher D. G., Saunders N. A., Owen R. J.; Rapid extraction of bacterial genomic DNA with guanidium thiocyanate; Lett. Appl. Microbiol.; 1989; vol. 8; pp. 151–156.

Dretzen G., Bellard M., Sassone-Corsi P., Chambon P.; A reliable method for the recovery of DNA fragments from agarose and acrylamide gels; Anal. Biochem.; 1981; vol. 112; pp. 295–298.

TABLE 3

Detergents and wash conditions.

| Area | Detergent | Det. Dose g/l | Inactivation | Enzyme dose mg/l | Temp. ° C. | Time min | pH | Water hardness °dH | Ca:Mg |
|---|---|---|---|---|---|---|---|---|---|
| A/P | Model detergent 97 | 3 | – | 1 | 25 | 15 | 10.5 | 6 | 2:1 |
| Latin America | Omo Multi Acao | 3 | – | 1 | 25 | 15 | 10.6 | 6 | 2:1 |
| Europe | Omo conc. powder | 4 | + | 0.2 | 40 | 30 | 10.2 | 15 | 4:1 |
| Europe | Ariel Futur liquid | 5 | + | 0.2 | 40 | 30 | 9.0 | 15 | 4:1 |

What is claimed is:

1. An isolated polypeptide having alpha-amylase activity, comprising a polypeptide having an amino acid sequence which has at least 85% identity with amino acids 1 to 485 of SEQ ID NO:2 or SEQ ID NO:4.

2. The isolated polypeptide of claim 1, comprising the amino acid sequence of SEQ ID NO:2.

3. The isolated polypeptide of claim 1, comprising the amino acid sequence of SEQ ID NO:4.

4. The isolated polypeptide of claim 1, consisting of the amino acid sequence of SEQ ID NO:2, or a fragment thereof.

5. The isolated polypeptide of claim 1, consisting of the amino acid sequence of SEQ ID NO:4, or a fragment thereof.

6. The isolated polypeptide of claim 1, consisting of amino acids 1 to 485 of SEQ ID NO:2 or SEQ ID NO:4.

* * * * *